(12) United States Patent
Sakamoto et al.

(10) Patent No.: US 7,524,978 B2
(45) Date of Patent: Apr. 28, 2009

(54) 2-OXABICYCLO[3.3.0]OCTANE COMPOUNDS, PROCESS FOR PRODUCING THE SAME, OPTICAL RESOLVER, METHOD OF SEPARATING DIASTEREOMER MIXTURE, AND METHOD OF OPTICALLY RESOLVING ALCOHOL

(75) Inventors: Kei Sakamoto, Tokyo (JP); Yasushi Nakano, Tokyo (JP); Yoshihisa Kondou, Tokyo (JP); Toshiro Yamada, Tokyo (JP); Hisao Nemoto, Tokushima (JP)

(73) Assignee: Zeon Corporation, Tokyo (JP)

( * ) Notice: Subject to any disclaimer, the term of this patent is extended or adjusted under 35 U.S.C. 154(b) by 92 days.

(21) Appl. No.: 10/520,282

(22) PCT Filed: Aug. 22, 2003

(86) PCT No.: PCT/JP03/10643

§ 371 (c)(1),
(2), (4) Date: Feb. 22, 2006

(87) PCT Pub. No.: WO2004/018445

PCT Pub. Date: Mar. 4, 2004

(65) Prior Publication Data

US 2006/0205960 A1    Sep. 14, 2006

(30) Foreign Application Priority Data

Aug. 23, 2002 (JP) ............................. 2002-244371
Aug. 23, 2002 (JP) ............................. 2002-244374

(51) Int. Cl.
C07D 307/937 (2006.01)
(52) U.S. Cl. ...................................... 549/465
(58) Field of Classification Search ................... 549/465
See application file for complete search history.

(56) References Cited

U.S. PATENT DOCUMENTS 5,344,942 A    9/1994    Noe et al.
2004/0077098 A1    4/2004    Nemoto et al.

FOREIGN PATENT DOCUMENTS

EP    565969 A1    10/1993
WO    02/072505 A1    9/2002

OTHER PUBLICATIONS

Semmelhack et al., J. Am. Chem. Soc. (1982), vol. 104(3), pp. 747-759.*
K.S. Feldman, et al.; "Intramolecular Bicyclization of Hydroxypentynyliodonium Triflate Derivatives to Furnish Cyclopentannelated Tetrahydrofurans: The First Examples of Cyclopentene Formation Following Alkoxide Addition to Alkynyliodonium Salts;" Tetrahedron Letters; vol. 39; 1998; pp. 2911-2914.
J. Leitich, et al.; "The Addition of 2-Oxido-2-cyclopenten-1-ylium to Some Olefins and Dienes in 2,2,2-Trifluoroethanol;" Eur. J. Org. Chem.; 2001; pp. 2707-2718.
L. Fensterbank, et al.; "Variations on Radical Cascades of Vinyl Radicals Generated from Bromomethyldimethylsilyl Propargyl Ethers;" Tetrahedron; vol. 52; No. 35; 1996; pp. 11405-11420.
A. R. Daniewski, et al.; "Baeyer-Villiger Oxidation of (3aS and 3aR, 7aS)-1, 2, 3a, 4, 5, 6, 7, 7a-octahydro-7a-Methyl [1H]inden-1,5-diones. Synthesis of a Chiral Synthon for Total Synthesis of 14β-Estrone;" Bulletin of the Polish Academy of Sciences, Chemistry; vol. 37; No. 7-8; 1989; pp. 277-281.
A. R. Daniewski, et al.; "A New Route to a Chiral Synthon for the Total Synthesis of Estrone;" Synthesis; Aug. 1987; pp. 705-708.
D. R. Morton, et al; "Molecular Photochemistry. XXVII. Photochemical Ring Expansion of Cyclobutanone, Substituted Cyclobutanones, and Related Cyclic Ketones;" Journal of the American Chemical Society; vol. 92; No. 14; Jul. 15, 1970; pp. 4349-4357 and Cover Sheet.
H. Nemoto; "A New Alkenyl Ether Giving Acetal with Stereospecific Manner;" Tetrahedron Letters; vol. 35; No. 42; 1994; pp. 7785-7788.

* cited by examiner

Primary Examiner—Taofiq A Solola
(74) Attorney, Agent, or Firm—Kratz, Quintos & Hanson, LLP

(57) ABSTRACT

2-Oxabicyclo[3.3.0]octane compounds represented by the following formula (1) (compound (1)); an optical resolver comprising at least one of the compounds (1); a process for producing the compounds (1) which comprises reacting a compound (2) or compound (3) with an alcohol (5) in the presence of an acid catalyst; a method of separating a diastereomer mixture of a compound (1); and a method of optically resolving an alcohol with the optical resolver.

[In the formulae, $R^1$ to $R^{10}$ each represents hydrogen atom, etc.; $R^{11}$ represents an alkyl group, etc.; $R^{12}$ represents a hydrocarbon group, etc.; $R^{13}$ represents a hydrocarbon group, etc.; and A represents acetyl group, etc.]

12 Claims, 1 Drawing Sheet

2-OXABICYCLO[3.3.0]OCTANE COMPOUNDS, PROCESS FOR PRODUCING THE SAME, OPTICAL RESOLVER, METHOD OF SEPARATING DIASTEREOMER MIXTURE, AND METHOD OF OPTICALLY RESOLVING ALCOHOL

TECHNICAL FIELD

The present invention provides a compound having a 2-oxabicyclo[3.3.0]octane skeleton with a hydrocarbon group bonded to position 1 via an oxygen atom and a substituent selected from various groups such as hydrogen, alkoxycarbonyl, and the like bonded to position 5 (hereinafter referred to as 2-oxabicyclo[3.3.0]octane compound), a process for producing the compound, an optical resolving agent, a method of separating a diastereomer mixture, and a method of optically resolving alcohol using the optical resolving agent.

BACKGROUND ART

Many physiologically active substances such as pharmaceuticals, agricultural chemicals, perfumes, and sweeteners are alcohols having an asymmetric carbon atom or compounds having a partial structure of such an alcohol (hereinafter referred to simply as "alcohols"). There may be optical isomers in such a compound. However, there may be a significant difference in the degree of physiological activity among these optical isomers. Some isomers exhibit physiological activity quite different from others. Therefore, development of a method for separating an optical isomer mixture of alcohols easily without failure has been desired.

As an example of optically resolving an alcohol, Synlett., (6), 862 (2000), J. Org. Chem., 64, 2638 (1999), and the like describe a method comprising allowing one of optical isomers to remain as the alcohol and transforming the other optical isomer into an ester derivative in a natural optically active environment (for example, internal organs of animals containing an esterified enzyme or hydrolyzed enzyme). However, since such an enzyme does not have chemical stability, in particular, thermal stability, the enzyme cannot be used under high temperature conditions. Further, it is difficult for the enzyme to be generally and widely accepted due to its high cost and difficulty in being procured in a large amount.

Tetrahedron., Lett., 35, 4397 (1994) reported an experiment in which an ester prepared by condensing a carboxylic acid having an asymmetric carbon atom with an alcohol was separated into individual diastereomers by silica gel column chromatography. In principle, this is optical resolution of an alcohol.

However, since there are no general rules or principles for producing a highly separable diastereomer mixture, the method cannot be generally applied. And the mixture can rarely be separated into two optical isomers without being influenced by an external optically active factor, such as in the case of spontaneous resolution. General rules for separation do not exist. Accordingly, in almost all cases, it is highly difficult to speculate whether or not an optical isomer mixture of alcohol and the like can be separated into optically active compounds. The mixture is not easily separated in almost all cases.

The present invention has been achieved in view of this situation and has an objective of providing a novel 2-oxabicyclo[3.3.0]octane compound which can be used as an optical resolving agent of an optical isomer mixture such as alcohol, a process for producing such a compound, an optical resolving agent containing at least one 2-oxabicyclo[3.3.0]octane compound, a method of separating a diastereomer mixture, and a method of optically resolving alcohol using the optical resolving agent.

DISCLOSURE OF THE INVENTION

Figure 1:
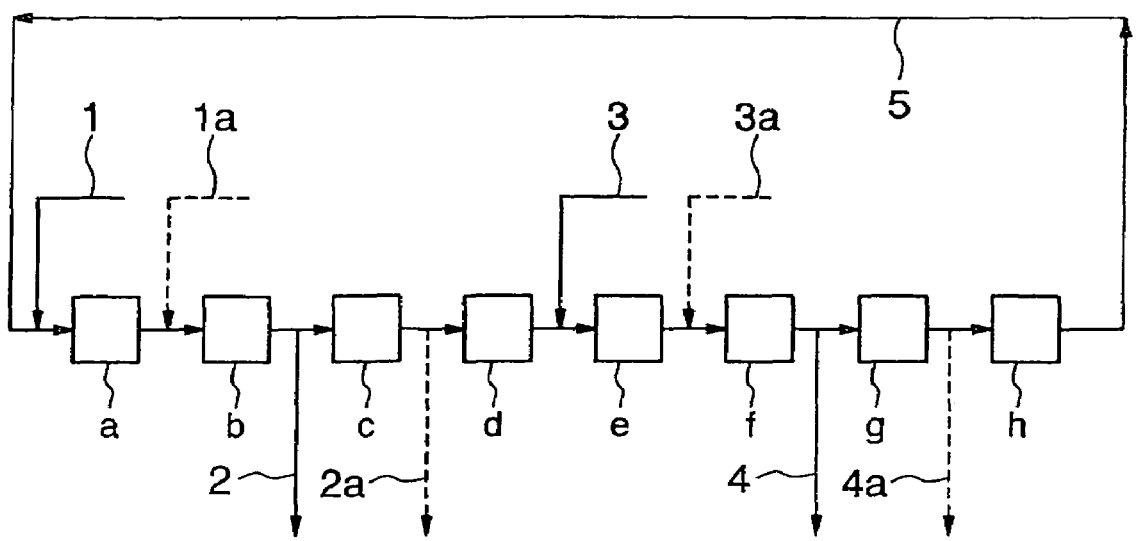
FIG. 1 is a flow chart showing a flow of fluid in a simulated moving bed chromatographic separation apparatus used in the present invention.

The present inventors previously reported that 1-alkoxy-5-(2-propenyl)-2-oxabicyclo[3.3.0]octane and the like represented by the formula (A) can be used as an optical resolution agent of an optical isomer mixture such as alcohol (WO02/072505 (PCT/JP02/01644)).

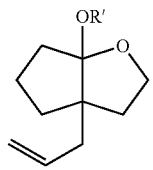

(A)

wherein R' represents a methyl group or the like.

The present inventors have conducted extensive studies to obtain a 2-oxabicyclo[3.3.0]octane compound which has various substituents at position 5 of the 2-oxabicyclo[3.3.0]octane ring as an analogue of the compound represented by the formula (A). As a result, the present inventors have found that a 2-oxabicyclo[3.3.0]octane compound which has a hydrogen atom, an alkoxycarbonyl group, or the like bonded to position 5 of the 2-oxabicyclo[3.3.0]octane ring can be prepared efficiently by a reaction of a cyclopentanone compound having a 2-acetoxyethyl group and a substituent such as a hydrogen atom or an alkoxycarbonyl group at position 2 of a cyclopentanone ring, with an alcohol in the presence of an acid catalyst, and that this compound can be used as an optical resolving agent for an optical isomer mixture such as alcohol.

The present inventors have further found that a diastereomer mixture of a 1-alkoxy-2-oxabicyclo[3.3.0]octane compound with a substituted or unsubstituted chiral hydrocarbon group bonded to position 1 of the 2-oxabicyclo[3.3.0]octane ring via an oxygen atom can be efficiently separated into individual diastereomers by simulated moving bed chromatography or distillation, and that an alcohol having an asymmetric carbon atom in the molecule can be optically resolved using the separated diastereomer. These findings led to the completion of the present invention.

The present invention thus provides a 2-oxabicyclo[3.3.0]octane compound of the formula (1):

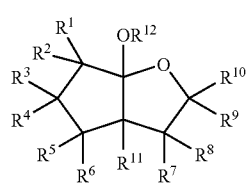

(1)

wherein $R^1$-$R^{10}$ individually represent a hydrogen atom or a substituted or unsubstituted alkyl group having 1-20 carbon atoms, $R^{11}$ represents a hydrogen atom, a substituted or unsubstituted alkyl group, a substituted or unsubstituted alkynyl group, a substituted or unsubstituted cycloalkyl group, a substituted or unsubstituted cycloalkenyl group, a substituted or unsubstituted aryl group, formyl group, a substituted or unsubstituted acyl group, a substituted or unsubstituted alkoxycarbonyl group, a substituted or unsubstituted alkenyloxycarbonyl group, a substituted or unsubstituted aryloxycarbonyl group, or a substituted or unsubstituted alkenyl group, and $R^{12}$ represents a substituted or unsubstituted hydrocarbon group, provided that when $R^{11}$ is a substituted or unsubstituted alkenyl group, $R^{12}$ is a chiral group.

In the 2-oxabicyclo[3.3.0]octane compound of the present invention, the $R^{12}$ group is preferably a chiralic secondary hydrocarbon group which may have a substituent, and more preferably a chiralic secondary hydrocarbon group having a crosslinked structure or a chiralic secondary alkyl group substituted with an alkoxycarbonyl group.

The present invention further provides an optical resolution agent comprising at least one 2-oxabicyclo[3.3.0]octane compound of the formula (1):

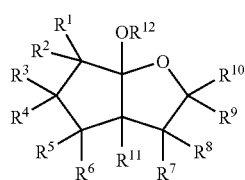

(1)

wherein $R^1$-$R^{10}$ individually represent a hydrogen atom or a substituted or unsubstituted alkyl group having 1-20 carbon atoms, $R^{11}$ represents a hydrogen atom, a substituted or unsubstituted alkyl group, a substituted or unsubstituted alkynyl group, a substituted or unsubstituted cycloalkyl group, a substituted or unsubstituted cycloalkenyl group, a substituted or unsubstituted aryl group, formyl group, a substituted or unsubstituted acyl group, a substituted or unsubstituted alkoxycarbonyl group, a substituted or unsubstituted alkenyloxycarbonyl group, a substituted or unsubstituted aryloxycarbonyl group, or a substituted or unsubstituted alkenyl group, and $R^{12}$ represents a substituted or unsubstituted hydrocarbon group, provided that when $R^{11}$ is a substituted or unsubstituted alkenyl group, $R^{12}$ is a chiral group.

The present invention further provides a process for producing a 2-oxabicyclo[3.3.0]octane compound represented by the above formula (1) comprising reacting a cyclopentanone compound of the formula (2),

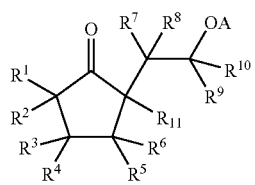

(2)

wherein the $R^1$-$R^{11}$ groups are the same as in the formula (1) and A represents a hydrogen atom or a protective group for a hydroxyl group, with an optically active alcohol of the formula $R^{12}OH$, wherein $R^{12}$ is the same as in the formula (1), in the presence of an acid catalyst.

The present invention further provides a process for producing a 2-oxabicyclo[3.3.0]octane compound represented by the above formula (1) comprising reacting a 2-oxabicyclo[3.3.0]octane compound of the formula (3),

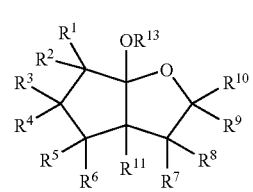

(3)

wherein the $R^1$-$R^{11}$ groups are the same as in the formula (1) and $R^{13}$ is a substituted or unsubstituted hydrocarbon group, with an alcohol of the formula $R^{12}OH$, wherein $R^{12}$ is as defined above, in the presence of an acid catalyst.

The present invention further provides a method for separating a diastereomer mixture of 2-oxabicyclo[3.3.0]octane compound of the above formula (1) comprising processing the diastereomer mixture of 2-oxabicyclo[3.3.0]octane compound of the above formula (1) using a simulated moving bed chromatography to separate into individual diastereomers.

The present invention further provides a method for separating a diastereomer mixture of 2-oxabicyclo[3.3.0]octane compound of the above formula (1) comprising distilling the diastereomer mixture of 2-oxabicyclo[3.3.0]octane compound of the above formula (1) to separate into individual diastereomers.

The present invention further provides a method of optically resolving alcohol of the formula $R^{14}OH$, wherein $R^{14}$ represents a substituted or unsubstituted hydrocarbon group having an asymmetric carbon atom, comprising, a step of separating a diastereomer mixture of 2-oxabicyclo[3.3.0]octane compound of the above formula (1) into individual diastereomers, a step of reacting the separated diastereomers with an alcohol of the formula $R^{13}OH$, wherein $R^{13}$ is a substituted or unsubstituted hydrocarbon group, in the presence of an acid catalyst to obtain a 2-oxabicyclo[3.3.0]octane compound of the formula (3),

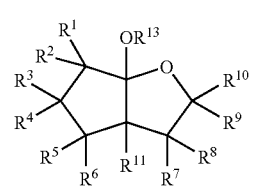

(3)

wherein $R^1$-$R^{11}$ are the same as in the formula (1) and $R^{13}$ is as defined above, a step of reacting the compound of the formula (3) with an optical isomer mixture of alcohol of the formula $R^{14}OH$, wherein $R^{14}$ is as defined above, in the presence of an acid catalyst to obtain a diastereomer mixture of the formula (4),

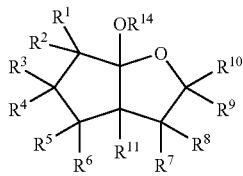
(4)

wherein $R^1$-$R^{11}$ and $R^{14}$ are the same as defined above, a step of separating the resulting diastereomer mixture into individual diastereomers, and a step of reacting the separated diastereomers with an alcohol of the formula, $R^{15}OH$, wherein $R^{15}$ represents a substituted or unsubstituted hydrocarbon group, in the presence of an acid catalyst to obtain an optically active alcohol of the formula $R^{14}OH$, wherein $R^{14}$ is as defined above.

In the optical resolution method of alcohol in the present invention, the step of separating the diastereomer mixture of the compound of the above formula (4) into individual diastereomers preferably comprises processing the diastereomer mixture using a simulated moving bed chromatography to separate into individual diastereomers or distilling the diastereomer mixture to separate into individual diastereomers.

In the optical resolution method of alcohol of the present invention, it is preferable to isolate the compound of the above formula (3) from the optical active alcohol of the formula $R^{14}OH$, wherein $R^{14}$ is as defined above, by reacting the separated diastereomer of the compound of the formula (4) with an alcohol of the formula $R^{13}OH$, wherein $R^{13}$ is as defined above, in the presence of an acid catalyst, and to reuse the isolated compound of the formula (3) as an optical resolution agent of alcohol.

BEST MODE FOR CARRYING OUT THE INVENTION

The present invention will be described in detail in the following sections: (1) 2-oxabicyclo[3.3.0]octane compound, (2) process for producing 2-oxabicyclo[3.3.0]octane compound, (3) optical resolution agent, (4) method for separating a diastereomer mixture, and (5) optical resolution method of alcohol.

(1) 2-oxabicyclo[3.3.0]octane compound

In the first place, the present invention provides a 2-oxabicyclo[3.3.0]octane compound of the above formula (1).

In the above formula, $R^1$-$R^{10}$ individually represent a hydrogen atom or a substituted or unsubstituted alkyl group having 1-20 carbon atoms.

Examples of the alkyl group having 1-20 carbon atoms include a methyl group, ethyl group, n-propyl group, isopropyl group, n-butyl group, sec-butyl group, isobutyl group, n-pentyl group, n-hexyl group, n-octyl group, n-nonyl group, and n-decyl group. Examples of the substituent for these groups include a hydroxyl group; alkoxy groups such as a methoxy group and ethoxy group; alkylthio groups such as a methylthio group and ethylthio group; halogen atoms such as a fluorine atom and chlorine atom; and substituted or unsubstituted phenyl groups such as a phenyl group, 2-chlorophenyl group, 3-methoxyphenyl group, and 4-methylphenyl group. Of these, a compound in which $R^1$-$R^{10}$ are individually a hydrogen atom or a methyl group is preferable, since the compound can be easily made available or produced. A compound in which all $R^1$-$R^{10}$ groups are a hydrogen atom is particularly preferable.

$R^{11}$ represents a hydrogen atom, a substituted or unsubstituted alkyl group, a substituted or unsubstituted alkynyl group, a substituted or unsubstituted cycloalkyl group, a substituted or unsubstituted cycloalkenyl group, a substituted or unsubstituted aryl group, formyl group, a substituted or unsubstituted acyl group, a substituted or unsubstituted alkoxycarbonyl group, a substituted or unsubstituted alkenyloxycarbonyl group, a substituted or unsubstituted aryloxycarbonyl group, or a substituted or unsubstituted alkenyl group. When $R^{11}$ is a group other than a hydrogen atom, the number of carbon atoms in such a group is preferably 1-20.

Examples of the alkyl group represented by $R^{11}$ include a methyl group, ethyl group, n-propyl group, isopropyl group, n-butyl group, sec-butyl group, t-butyl group, n-pentyl group, and n-hexyl group.

As examples of the alkynyl group, an ethynyl group, propargyl group, and 1-butynyl group can be given.

Examples of the cycloalkyl group include a cyclopropyl group, cyclopentyl group, cyclohexyl group, and cyclooctyl group.

Examples of the cycloalkenyl group include a cyclopentenyl group, cyclohexenyl group, and cyclooctenyl group.

Examples of the aryl group include a phenyl group, 1-naphthyl group, and 2-naphthyl group.

There are no specific limitations to the substituents of the alkyl group, alkynyl group, cycloalkyl group, cycloalkenyl group, and aryl group inasmuch as the substituents are stable in an acid. As examples, an alkoxy group, alkoxycarbonyl group, hydroxyl group, acyl group, nitro group, cyano group, halogen atom, phenyl group, and heterocyclic group can be given. There are no specific limitations to the position for these substituents. Two or more substituents, either the same or different, may bond with a hydrocarbon group.

Examples of the substituted or unsubstituted acyl group include an acetyl group, propionyl group, butyryl group, benzoyl group, 4-methylbenzoyl group, and 2,4,6-trimethylbenzoyl group.

Examples of the alkoxycarbonyl group include a methoxycarbonyl group, ethoxycarbonyl group, n-propoxycarbonyl group, isopropoxycarbonyl group, n-butoxycarbonyl group, sec-butoxycarbonyl group, tert-butoxycarbonyl group, n-pentyloxycarbonyl group, and n-hexyloxycarbonyl group.

Examples of the alkenyloxycarbonyl group include a vinyloxycarbonyl group, 1-propenyloxycarbonyl group, 2-propenyloxycarbonyl group, isopropenyloxycarbonyl group, 2-butenyloxycarbonyl group, methallyloxycarbonyl group, 2-pentenyloxycarbonyl group, and 2-hexenyloxycarbonyl group.

Examples of the aryloxycarbonyl group include a phenoxycarbonyl group, 1-naphthyloxycarbonyl group, and 2-naphthyloxycarbonyl group.

As examples of the substituents for the alkoxycarbonyl group, alkenyloxycarbonyl group, and aryloxycarbonyl group, a halogen atom, alkoxy group, alkylthio group, alkylsulfonyl group, cyano group, nitro group, substituted or unsubstituted phenyl group, and substituted or unsubstituted heterocyclic group can be given. There are no specific limitations to the positions of these substituents. Two or more substituents, either the same or different, may bond to one group.

As examples of the alkenyl group, a vinyl group, 1-propenyl group, 2-propenyl group, isopropenyl group, 1-butenyl group, 2-butenyl group, 3-butenyl group, methallyl group, 1-pentenyl group, 2-pentenyl group, 3-pentenyl group, 1-hexenyl group, 2-hexenyl group, 3-hexenyl group, 1-heptenyl group, 2-heptenyl group, 5-heptenyl group, 1-octenyl group, 3-octenyl group, and 5-octenyl group can be given.

There are no specific limitations to the substituents on the alkenyl group inasmuch as the compound is stable against an acid catalyst. As examples, a haloalkyl group, cycloalkyl group, alkoxy group, alkoxycarbonyl group, alkylthio group, alkylsulfonyl group, acyl group, nitro group, cyano group, hydroxyl group, halogen atom, substituted or unsubstituted phenyl group, and substituted or unsubstituted heterocyclic group can be given. There are no specific limitations to the positions of these substituents. Two or more substituents, either the same or different, may bond to one group.

As examples of the substituted or unsubstituted alkenyl group, an aklenyl group such as a vinyl group, 1-propenyl group, 2-propenyl group, isopropenyl group, 1-butenyl group, 2-butenyl group, 3-butenyl group, methallyl group, 1-pentenyl group, 2-pentenyl group, and 2-ethyl-2-butenyl group; cinnamyl group, 4-chlorocinnamyl group, and 2-methylcinnamyl group can be given.

Of these, for the reasons of easy availability and easy manufacturing, $R^{11}$ is preferably a hydrogen atom, substituted or unsubstituted alkyl group, substituted or unsubstituted alkoxycarbonyl group, substituted or unsubstituted alkenyloxycarbonyl group, substituted or unsubstituted aryloxycarbonyl group, or substituted or unsubstituted alkenyl group having 2-6 carbon atoms, more preferably a hydrogen atom, substituted or unsubstituted alkyl group, substituted or unsubstituted alkoxycarbonyl group, or substituted or unsubstituted alkenyl group having 2-6 carbon atoms, and particularly preferably a hydrogen atom, substituted or unsubstituted alkoxycarbonyl group, or 2-propenyl group.

$R^{12}$ represents a substituted or unsubstituted hydrocarbon group, preferably a substituted or unsubstituted hydrocarbon group having 1-20 carbon atoms. The hydrocarbon group may be a primary, secondary, or tertiary hydrocarbon group.

As the hydrocarbon group represented by $R^{12}$, an alkyl group, alkenyl group, alkynyl group, cycloalkyl group, cycloalkenyl group, and hydrocarbon group having a bridged structure (a structure in which two points not adjoining each other in a cyclic structure are bridged via one or more atoms) can be given.

As examples of the alkyl group represented by $R^{12}$, a methyl group, ethyl group, n-propyl group, isopropyl group, n-butyl group, isobutyl group, sec-butyl group, t-butyl group, n-pentyl group, isopentyl group, neopentyl group, n-hexyl group, isohexyl group, n-heptyl group, n-octyl group, n-nonyl group, n-decyl group, n-undecyl group, and n-dodecyl group can be given. As examples of the alkenyl group, 1-propenyl group, 2-propenyl group, 1-butenyl group, 2-butenyl group, 3-butenyl group, 1-pentenyl group, 2-pentenyl group, 3-pentenyl group, 4-pentenyl group, 1-hexenyl group, 2-hexenyl group, 3-hexenyl group, 4-hexenyl group, 5-hexenyl group, 1-heptenyl group, 2-heptenyl group, 5-heptenyl group, 6-heptenyl group, 1-octenyl group, 2-octenyl group, 4-octenyl group, and 7-octenyl group can be given.

As examples of the alkynyl group, a 1-propynyl group, 2-propynyl group, 1-butynyl group, 2-butynyl group, 3-butynyl group, 1-pentynyl group, 2-pentynyl group, 4-pentynyl group, 1-hexynyl group, 2-hexynyl group, 5-hexynyl group, 1-heptynyl group, 2-heptynyl group, 4-heptynyl group, 6-heptynyl group, and 1-octynyl group can be given.

Examples of the cycloalkyl group include cycloalkyl groups such as a cyclopropyl group, cyclobutyl group, cyclopentyl group, cyclohexyl group, cycloheptyl group, and cyclooctyl group.

Examples of the cycloalkenyl group include cycloalkenyl groups such as 2-cyclopentenyl group, 3-cyclopentenyl group, 2-cyclohexenyl group, 3-cyclohexenyl group, 2-cycloheptenyl group, and 3-cyclooctenyl group. As examples of the hydrocarbon group having a bridged structure, bicyclo[2.1.0]pentyl group, bicyclo[4.1.0]heptan-3-yl group, bicyclo[2.2.1]heptan-2-yl group, and bicyclo[3.2.1]octan-6-yl group can be given.

As examples of the substituent for the hydrocarbon group represented by $R^{12}$, a haloalkyl group, alkoxy group, alkoxycarbonyl group, alkylthio group, alkylsulfonyl group, acyl group, acylamino group, nitro group, cyano group, halogen atom, silyl group, substituted or unsubstituted phenyl group, and substituted or unsubstituted heterocyclic group can be given. As examples of the substituent for the phenyl group or the heterocyclic group, halogen atoms such as fluorine and chlorine; alkyl groups such as a methyl group and ethyl group; alkoxy groups such as a methoxy group and ethoxy group; a cyano group; and a nitro group can be given. There are no specific limitations to the positions of these substituents. Two or more substituents, either the same or different, may bond to the hydrocarbon group.

Although $R^{12}$ may be either a group having an asymmetric carbon atom or a group not having an asymmetric carbon atom, when $R^{11}$ is a substituted or unsubstituted alkenyl group. However, $R^{12}$ is a chiral group having at least one asymmetric carbon atom. When $R^{12}$ is a group having an asymmetric carbon atom, the number of the asymmetric carbon atoms may be either one or two or more, and there are no specific limitations to the positions of the asymmetric carbon atoms.

When $R^{12}$ is a chiral hydrocarbon group, $R^{12}$ may be a primary, secondary, or tertiary hydrocarbon group. $R^{12}$ is preferably a secondary hydrocarbon group, and particularly preferably a secondary hydrocarbon group having 1-15 carbon atoms.

When $R^{12}$ is a substituted or unsubstituted chiral secondary hydrocarbon group, $R^{12}$ is more preferably a chiral secondary hydrocarbon group having a bridged structure or a chiral secondary alkyl group substituted with an alkoxycarbonyl group. More preferable groups are a chiral 2-isopropyl-5-methyl-cyclohexyl group (menthyl group), a chiral 1,7,7-trimethylbicyclo[2.2.1]heptan-2-yl group (bornyl group), and chiral 1-ethoxycarbonylethyl group, with a chiral 1,7,7-trimethylbicyclo[2.2.1]heptan-2-yl group (bornyl group) or a chiral 1-ethoxycarbonylethyl group being particularly preferable.

Specific examples of the 2-oxabicyclo[3.3.0]octane compound represented by the formula (1) include:
2-oxabicyclo[3.3.0]octane compounds in which $R^{11}$ is a hydrogen atom such as
1-methoxy-2-oxabicyclo[3.3.0]octane, 1-ethoxy-2-oxabicyclo[3.3.0]octane,
1-sec-butoxy-2-oxabicyclo[3.3.0]octane,
1-(1-methyloctyloxy)-2-oxabicyclo[3.3.0]octane,
1-(1-trifluoromethylpropoxy)-2-oxabicyclo[3.3.0]octane,
1-(d)-bornyloxy-2-oxabicyclo[3.3.0]octane, 1-(1 )-bornyloxy-2-oxabicyclo[3.3.0]octane,
1-(1-(S)-ethoxycarbonyl)ethoxy-2-oxabicyclo[3.3.0]octane,
1-(1-(R)-ethoxycarbonyl)ethoxy-2-oxabicyclo[3.3.0]octane,
1-(1)-mentyloxy-2-oxabicyclo[3.3.0]octane, and
1-(d)-menthyloxy-2-oxabicyclo[3.3.0]octane;
2-oxabicyclo[3.3.0]octane compounds in which $R^{11}$ is a substituted or unsubstituted alkyl group such as 1-methoxy-5-methyl-2-oxabicyclo[3.3.0]octane,
1-methoxy-5-ethyl-2-oxabicyclo[3.3.0]octane,
1-methoxy-5-n-propyl-2-oxabicyclo[3.3.0]octane, 1-methoxy-5-isopropyl-2-oxabicyclo[3.3.0]octane,
1-methoxy-5-n-butyl-2-oxabicyclo[3.3.0]octane,
1-methoxy-5-tert-butyl-2-oxabicyclo[3.3.0]octane,
1-methoxy-5-n-pentyl-2-oxabicyclo[3.3.0]octane,
1-methoxy-5-n-hexyl-2-oxabicyclo[3.3.0]octane,
1-methoxy-5-benzyl-2-oxabicyclo[3.3.0]octane,
1-methoxy-5-(2-phenylethyl)-2-oxabicyclo[3.3.0]octane,
1-methoxy-5-methoxymethyl-2-oxabicyclo[3.3.0]octane,
1-methoxy-5-methylthiomethyl-2-oxabicyclo[3.3.0]octane,
1-methoxy-5-methylsulfonyl-2-oxabicyclo[3.3.0]octane,
1-methoxy-5-cyanomethyl-2-oxabicyclo[3.3.0]octane,
1-methoxy-5-chloromethyl-2-oxabicyclo[3.3.0]octane,
1-methoxy-5-trimethylsilylmethyl-2-oxabicyclo[3.3.0]octane,
1-methoxy-5-methoxycarbonylmethyl-2-oxabicyclo[3.3.0]octane,
1-ethoxy-5-methyl-2-oxabicyclo[3.3.0]octane,
1-sec-butoxy-5-methyl-2-oxabicyclo[3.3.0]octane,
1-(1-methyloctyloxy)-5-methyl-2-oxabicyclo[3.3.0]octane,
1-(1-trifluoromethyl-n-propoxy)-5-methyl-2-oxabicyclo[3.3.0]octane,
1-(d)-bornyloxy-5-methyl-2-oxabicyclo[3.3.0]octane,
1-(l)-bornyloxy-5-methyl-2-oxabicyclo[3.3.0]octane,
1-(1-(S)-ethoxycarbonyl)ethoxy-5-methyl-2-oxabicyclo[3.3.0]octane,
1-(1-(R)-ethoxycarbonyl)ethoxy-5-methyl-2-oxabicyclo[3.3.0]octane,
1-(l)-mentyloxy-5-methyl-2-oxabicyclo[3.3.0]octane,
1-(d)-mentyloxy-5-methyl-2-oxabicyclo[3.3.0]octane,
1-methoxy-5-diphenylmethyl-2-oxabicyclo[3.3.0]octane,
1-ethoxy-5-diphenylmethyl-2-oxabicyclo[3.3.0]octane,
1-(d)-bornyloxy-5-diphenylmethyl-2-oxabicyclo[3.3.0]octane,
1-(l)-bornyloxy-5-diphenylmethyl-2-oxabicyclo[3.3.0]octane,
1-(1-(S)-ethoxycarbonyl)ethoxy-5-diphenylmethyl-2-oxabicyclo[3.3.0]octane,
1-(1-(R)-ethoxycarbonyl)ethoxy-5-diphenylmethyl-2-oxabicyclo[3.3.0]octane,
1-(l)-mentyloxy-5-diphenylmethyl-2-oxabicyclo[3.3.0]octane, and
1-(d)-mentylloxy-5-diphenylmethyl-2-oxabicyclo[3.3.0]octane;
2-oxabicyclo[3.3.0]octane compounds in which $R^{11}$ is a substituted or unsubstituted cycloalkyl group such as 1-methoxy-5-cyclopropyl-2-oxabicyclo[3.3.0]octane,
1-methoxy-5-cyclopentyl-2-oxabicyclo[3.3.0]octane,
1-methoxy-5-cyclohexyl-2-oxabicyclo[3.3.0]octane,
1-ethoxy-5-cyclopentyl-2-oxabicyclo[3.3.0]octane,
1-sec-butoxy-5-cyclopentyl-2-oxabicyclo[3.3.0]octane,
1-(1-methyloctyloxy)-5-cyclopentyl-2-oxabicyclo[3.3.0]octane,
1-(1-trifluoromethylpropoxy)-5-cyclopentyl-2-oxabicyclo[3.3.0]octane,
1-(d)-bornyloxy-5-cyclopentyl-2-oxabicyclo[3.3.0]octane,
1-(l)-bornyloxy-5-cyclopentyl-2-oxabicyclo[3.3.0]octane,
1-(1-(S)-ethoxycarbonyl)ethoxy-5-cyclopentyl-2-oxabicyclo[3.3.0]octane,
1-(1-(R)-ethoxycarbonyl)ethoxy-5-cyclopentyl-2-oxabicyclo[3.3.0]octane,
1-(l)-mentyloxy-5-cyclopentyl-2-oxabicyclo[3.3.0]octane, and
1-(d)-mentyloxy-5-cyclopentyl-2-oxabicyclo[3.3.0]octane;
2-oxabicyclo[3.3.0]octane compounds in which $R^{11}$ is a substituted or unsubstituted cycloalkenyl group such as 1-methoxy-5-cyclopentenyl-2-oxabicyclo[3.3.0]octane,
1-methoxy-5-cyclohexenyl-2-oxabicyclo[3.3.0]octane,
1-ethoxy-5-cyclopentenyl-2-oxabicyclo[3.3.0]octane,
1-sec-butoxy-5-cyclohexenyl-2-oxabicyclo[3.3.0]octane,
1-(1-methyloctyloxy)-5-cyclopentenyl-2-oxabicyclo[3.3.0]octane,
1-(1-trifluoromethylpropoxy)-5-cyclohexenyl-2-oxabicyclo[3.3.0]octane,
1-(d)-bornyloxy-5-cyclohexenyl-2-oxabicyclo[3.3.0]octane,
1-(l)-bornyloxy-5-cyclohexenyl-2-oxabicyclo[3.3.0]octane,
1-(1-(S)-ethoxycarbonyl)ethoxy-5-cyclohexenyl-2-oxabicyclo[3.3.0]octane,
1-(1-(R)-ethoxycarbonyl)ethoxy-5-cyclohexenyl-2-oxabicyclo[3.3.0]octane,
1-(l)-mentyloxy-5-cyclohexenyl-2-oxabicyclo[3.3.0]octane, and
1-(d)-mentyloxy-5-cyclohexenyl-2-oxabicyclo[3.3.0]octane;
2-oxabicyclo[3.3.0]octane compounds in which $R^{11}$ is a substituted or unsubstituted alkynyl group such as 1-methoxy-5-ethynyl-2-oxabicyclo[3.3.0]octane,
1-methoxy-5-propargyl-2-oxabicyclo[3.3.0]octane,
1-ethoxy-5-propargyl-2-oxabicyclo[3.3.0]octane,
1-sec-butoxy-5-propargyl-2-oxabicyclo[3.3.0]octane,
1-(1-methyloctyloxy)-5-propargyl-2-oxabicyclo[3.3.0]octane,
1-(1-trifluoromethylpropoxy)-5-propargyl-2-oxabicyclo[3.3.0]octane,
1-(d)-bornyloxy-5-propargyl-2-oxabicyclo[3.3.0]octane,
1-(l)-bornyloxy-5-propargyl-2-oxabicyclo[3.3.0]octane,
1-(1-(S)-ethoxycarbonyl)ethoxy-5-propargyl-2-oxabicyclo[3.3.0]octane,
1-(1-(R)-ethoxycarbonyl)ethoxy-5-propargyl-2-oxabicyclo[3.3.0]octane,
1-(l)-mentyloxy-5-propargyl-2-oxabicyclo[3.3.0]octane, and
1-(d)-mentyloxy-5-propargyl-2-oxabicyclo[3.3.0]octane;
2-oxabicyclo[3.3.0]octane compounds in which $R^{11}$ is a substituted or unsubstituted aryl group such as 1-methoxy-5-phenyl-2-oxabicyclo[3.3.0]octane,
1-methoxy-5-(4-methylphenyl)-2-oxabicyclo[3.3.0]octane,
1-methoxy-5-(4-chlorophenyl)-2-oxabicyclo[3.3.0]octane,
1-methoxy-5-(2,4,6-trimethylphenyl)-2-oxabicyclo[3.3.0]octane,
1-methoxy-5-(1-naphthyl)-2-oxabicyclo[3.3.0]octane,
1-methoxy-5-(2-naphthyl)-2-oxabicyclo[3.3.0]octane,
1-ethoxy-5-phenyl-2-oxabicyclo[3.3.0]octane,
1-sec-butoxy-5-phenyl-2-oxabicyclo[3.3.0]octane,
1-(1'-methyloctyloxy)-5-phenyl-2-oxabicyclo[3.3.0]octane,
1-(1-trifluoromethylpropoxy)-5-phenyl-2-oxabicyclo[3.3.0]octane,
1-(d)-bornyloxy-5-phenyl-2-oxabicyclo[3.3.0]octane,
1-(l)-bornyloxy-5-phenyl-2-oxabicyclo[3.3.0]octane,
1-(1-(S)-ethoxycarbonyl)ethoxy-5-phenyl-2-oxabicyclo[3.3.0]octane,
1-(1-(R)-ethoxycarbonyl)ethoxy-5-phenyl-2-oxabicyclo[3.3.0]octane,
1-(l)-mentyloxy-5-phenyl-2-oxabicyclo[3.3.0]octane, and
1-(d)-mentyloxy-5-phenyl-2-oxabicyclo[3.3.0]octane;
2-oxabicyclo[3.3.0]octane compounds in which $R^{11}$ is a formyl group or a substituted or unsubstituted acyl group such as 1-methoxy-5-formyl-2-oxabicyclo[3.3.0]octane,
1-methoxy-5-acetyl-2-oxabicyclo[3.3.0]octane,
1-methoxy-5-propionyl-2-oxabicyclo[3.3.0]octane,
1-methoxy-5-benzoyl-2-oxabicyclo[3.3.0]octane, and
1-methoxy-5-(4-methylbenzoyl)-2-oxabicyclo[3.3.0]octane;

2-oxabicyclo[3.3.0]octane compounds in which $R^{11}$ is a substituted or unsubstituted alkoxycarbonyl group such as
1-methoxy-5-methoxycarbonyl-2-oxabicyclo[3.3.0]octane,
1-methoxy-5-ethoxycarbonyl-2-oxabicyclo[3.3.0]octane,
1-ethoxy-5-methoxycarbonyl-2-oxabicyclo[3.3.0]octane,
1-sec-butoxy-5-ethoxycarbonyl-2-oxabicyclo[3.3.0]octane,
1-(1-methyloctyloxy)-5-methoxycarbonyl-2-oxabicyclo[3.3.0]octane,
1-(1-trifluoromethylpropoxy)-5-methoxycarbonyl-2-oxabicyclo[3.3.0]octane,
1-(1-(S)-ethoxycarbonyl)ethoxy-5-methoxycarbonyl-2-oxabicyclo[3.3.0]octane,
1-(1-(R)-ethoxycarbonyl)ethoxy-5-methoxycarbonyl-2-oxabicyclo[3.3.0]octane,
1-(l)-mentyloxy-5-methoxycarbonyl-2-oxabicyclo[3.3.0]octane,
1-(d)-mentyloxy-5-methoxycarbonyl-2-oxabicyclo[3.3.0]octane,
1-(d)-bornyloxy-5-methoxycarbonyl-2-oxabicyclo[3.3.0]octane, and
1-(l)-bornyloxy-5-methoxycarbonyl-2-oxabicyclo[3.3.0]octane;
2-oxabicyclo[3.3.0]octane compounds in which $R^{11}$ is a substituted or unsubstituted alkenyloxycarbonyl group such as
1-methoxy-5-(2-propenyloxy)carbonyl-2-oxabicyclo[3.3.0]octane,
1-methoxy-5-isopropenyloxycarbonyl-2-oxabicyclo[3.3.0]octane,
1-methoxy-5-methallyloxycarbonyl-2-oxabicyclo[3.3.0]octane,
1-methoxy-5-cinnamyloxycarbonyl-2-oxabicyclo[3.3.0]octane,
1-(1-methyloctyloxy)-5-(2-propenyloxy)carbonyl-2-oxabicyclo[3.3.0]octane,
1-(1-trifluoromethylpropoxy)-5-(2-propenyloxy)carbonyl-2-oxabicyclo[3.3.0]octane,
1-(d)-bornyloxy-5-(2-propenyloxy)carbonyl-2-oxabicyclo[3.3.0]octane,
1-(l)-bornyloxy-5-(2-propenyloxy)carbonyl-2-oxabicyclo[3.3.0]octane,
1-(1-(S)-ethoxycarbonyl)ethoxy-5-(2-propenyloxy)carbonyl-2-oxabicyclo[3.3.0]octane,
1-(1-(R)-ethoxycarbonyl)ethoxy-5-(2-propenyloxy)carbonyl-2-oxabicyclo[3.3.0]octane,
1-(l)-mentyloxy-5-(2-propenyloxy)carbonyl-2-oxabicyclo[3.3.0]octane, and
1-(d)-mentyloxy-5-(2-propenyloxy)carbonyl-2-oxabicyclo[3.3.0]octane;
2-oxabicyclo[3.3.0]octane compounds in which $R^{11}$ is a substituted or unsubstituted aryloxycarbonyl group such as
1-methoxy-5-phenoxycarbonyl-2-oxabicyclo[3.3.0]octane,
1-methoxy-5-(4-methylphenoxy)carbonyl-2-oxabicyclo[3.3.0]octane,
1-methoxy-5-(1-naphthyloxycarbonyl)-2-oxabicyclo[3.3.0]octane, and
1-methoxy-5-(2-naphthyloxycarbonyl)-2-oxabicyclo[3.3.0]octane; and
2-oxabicyclo[3.3.0]octane compounds in which $R^{11}$ is a substituted or unsubstituted alkenyl group such as 1-(d)-bornyloxy-5-(2-propenyl)-2-oxabicyclo[3.3.0]octane,
1-(l)-bornyloxy-5-(2-propenyl)-2-oxabicyclo[3.3.0]octane,
1-(1-(S)-ethoxycarbonyl)ethoxy-5-(2-propenyl)-2-oxabicyclo[3.3.0]octane,
1-(1-(R)-ethoxycarbonyl)ethoxy-5-(2-propenyl)-2-oxabicyclo[3.3.0]octane,
1-(l)-mentyloxy-5-(2-propenyl)-2-oxabicyclo[3.3.0]octane, and
1-(d)-mentyloxy-5-(2-propenyl)-2-oxabicyclo[3.3.0]octane.

(2) Process for Producing 2-oxabicyclo[3.3.0]octane compound

In the second place, the present invention provides a process for producing 2-oxabicyclo[3.3.0]octane compound of the above formula (1) (hereinafter abbreviated as "2-oxabicyclo[3.3.0]octane compound (1)").

The 2-oxabicyclo[3.3.0]octane compound (1) can be produced by the following process (1) or process (2).

(i) Process (1)

The 2-oxabicyclo[3.3.0]octane compound (1) can be prepared by reacting a cyclopentanone compound of the formula (2) (hereinafter referred to as "cyclopentanone compound (2)") with an alcohol of the formula $R^{12}OH$ (hereinafter referred to as "alcohol (5)") in the presence of an acid catalyst. The target compound can be directly obtained from the cyclopentanone compound (2) by this process.

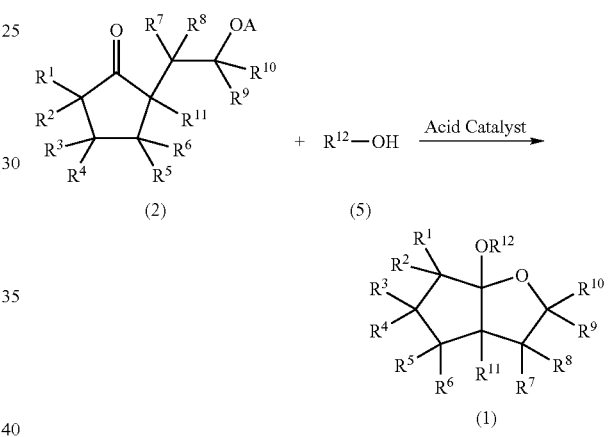

wherein $R^1$-$R^{12}$ are the same as defined above and A indicates a protective group of the hydroxyl group. As examples of the group A, a formyl group, acetyl group, propionyl group, benzoyl group, 4-chlorobenzoyl group, tert-butoxy carbonyl group, 2-tetrahydrofuranyl group, 2-tetrahydropyranyl group, 1-ethoxyethyl group, 1-ethoxyethoxy group, and tert-butyl can be given. Of these, due to easy availability and capability of producing the target compound at a high yield, an acetyl group and benzoyl group are preferable, with an acetyl group being particularly preferable.

The alcohol (5) usually has 1-20 carbon atoms, may be a primary, secondary, or tertiary alcohol, and either may have or may not have an asymmetric carbon atom in the molecule. However, when $R^{11}$ is a substituted or unsubstituted alkenyl group, the alcohol (5) is an optically active alcohol having an asymmetric carbon atom in the molecule.

When an optically active alcohol is used as the alcohol (5), a secondary alcohol is preferable, a secondary alcohol having 3-20 carbon atoms is more preferable due to easy availability and the capability of producing the target compound at a high yield.

As specific examples of the optically active secondary alcohol having 3-20 carbon atoms, menthols such as an optically active 2-isopropyl-5-methyl-cyclohexanol; lactic acid esters such as an optically active methyl lactate and optically active ethyl lactate; borneols such as an optically active 1-endo-borneol; synthetic perfumes such as isocamphylcyclohexanol; and the like can be given. Of these, (d)-menthol, (l)-menthol, (d)-borneol, (l)-borneol, (S)-methyl lactate, (R)-methyl lactate, (S)-ethyl lactate, and (R)-ethyl lactate are preferable due to their easy availability, with (d)-borneol, (l)-borneol, (S)-methyl lactate, (R)-methyl lactate, (S)-ethyl lactate, and (R)-ethyl lactate being particularly preferable.

Although there are no specific limitations to the amount of the alcohol (5), the alcohol (5) is usually used in an amount of 1-100 mols, and preferably 1-5 mols, for 1 mol of the cyclopentanone compound (2).

The reaction can be carried out by stirring a mixture of the cyclopentanone compound (2) and the alcohol (5) in a suitable solvent or without using a solvent in the presence of an acid catalyst. As the acid catalyst, either a liquid acid catalyst or a solid acid catalyst can be used without any specific limitations. For example, pyridinium p-toluenesulfonate (PPTS), p-toluenesulfonic acid (p-TsOH), montmorillonite, an acidic ion exchange resin, and synthetic zeolite (e.g. molecular sieve) can be given.

The acid catalyst is usually used in the amount of usually 0.0001-2 parts by weight, and preferably 0.001-1 part by weight, for 1 part by weight of the cyclopentanone compound (2).

The reaction can be carried out either without using a solvent or using an inert solvent.

There are no specific limitations to the solvent used for the reaction inasmuch as the solvent is nonprotonic. Examples of the solvent include aromatic hydrocarbons such as benzene, toluene, xylene, and chlorobenzene; aliphatic hydrocarbons such as n-pentane, n-hexane, n-heptane, n-octane, cyclohexane, methylcyclohexane, and petroleum ether; esters such as ethyl acetate, propyl acetate, and butyl acetate; halogenated hydrocarbons such as dichloromethane, chloroform, carbon tetrachloride, and 1,2-dichloroethane; ethers such as diethyl ether, dibutyl ether, tetrahydrofuran, 1,4-dioxane, 1,2-dimethoxyethane, cyclopentyl methyl ether, and anisole; and amides such as N,N-dimethylformamide, N,N-dimethylacetamide, and N-methylpyrrolidone. These solvents may be used either individually or in combination of two or more. Of these, an organic solvents having a comparatively low boiling point such as aromatic hydrocarbons, aliphatic hydrocarbons, and halogenated hydrocarbons are preferably used.

The reaction is smoothly carried out in the temperature range of −20° C. to the boiling point of the solvent used, and more preferably in the temperature range of −10° C. to 150° C. The reaction is completed usually in several minutes to several ten hours.

After the reaction and a common post treatment, the targeted 2-oxabicyclo[3.3.0]octane compound (1) can be obtained by known separating means such as column chromatography, distillation, and the like.

The cyclopentanone compound (2) used as the raw material can be produced according to the method described in Tetrahedron Lett., 35, 7785 (1994), for example.

A common production route is shown as follows.

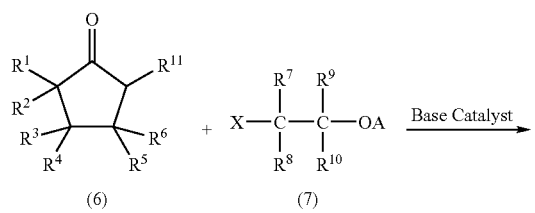

-continued

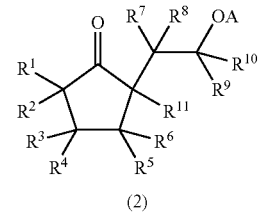

wherein $R^1$ to $R^{11}$ and A respectively represent the same groups as defined above and X represents a halogen atom such as chlorine, bromine, or iodine.

Specifically, the cyclopentanone compound (2) can be obtained by reacting a cyclopentanone compound of the formula (6) with a halogenated alkyl of the formula (7) in the presence of a base catalyst.

Among the compounds of the formula (1), the compound in which $R^{11}$ is a substituted or unsubstituted alkyl group can also be obtained from a compound in which $R^{11}$ is a substituted or unsubstituted alkenyl group by hydrogenating the carbon-carbon double bond of the alkenyl group. As the method of hydrogenation, a catalytic hydrogenation method using hydrogen in the presence of a hydrogenation catalyst can be given. There are no specific limitations to the hydrogenation catalyst. For example, a palladium catalyst such as palladium-carbon, Lindler catalyst, and palladium-alumina; platinum catalysts such as platinum oxide; ruthenium catalysts such as ruthenium-carbon; and the like can be given. In the hydrogenation reaction, common catalytic hydrogenation conditions can be used without any specific limitations.

(ii) Process (2)

The 2-oxabicyclo[3.3.0]octane compound (1) can be produced by reacting a compound of the formula (3) with an alcohol of the formula (5) in the presence of an acid catalyst.

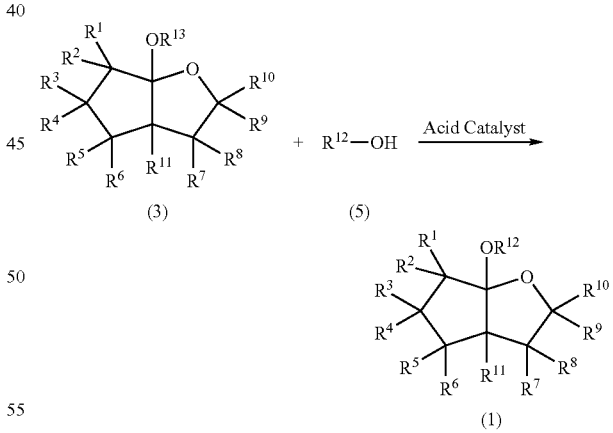

In the above formula, $R^{13}$ represents a substituted or unsubstituted hydrocarbon group. As examples of the hydrocarbon group represented by $R^{13}$, alkyl groups such as a methyl group, ethyl group, n-propyl group, isopropyl group, and n-butyl group; alkenyl groups such as a vinyl group, 1-propenyl group, 2-propenyl group, 1-butenyl group, and 2-butenyl group; alkynyl groups such as an ethynyl group, 1-propynyl group, 2-propynyl group, 1-butynyl group, and 2-butynyl group; cycloalkyl groups such as a cyclopropyl group, cyclopentyl group, cyclohexyl group, and cyclooctyl group;

cycloalkenyl groups such as a cyclopentenyl group, cyclohexenyl group, and cyclooctenyl group; and aryl groups such as a phenyl group, 1-naphthyl group, and 2-naphthyl group can be given.

There are no specific limitations to the substituent for the hydrocarbon group represented by $R^{13}$, inasmuch as such a group is stable against acid catalysts. Examples include an alkoxy group, alkoxycarbonyl group, alkylthio group, alkylsulfonyl group, acyl group, acylamino group, nitro group, cyano group, halogen atom, substituted or unsubstituted phenyl group, and substituted or unsubstituted heterocyclic group.

Of the above examples for $R^{13}$, due to easy removal of produced alcohols having the formula of $R^{13}OH$ from the reaction system, an alkyl group having 1-6 carbon atoms or an alkenyl group having 2-6 carbon-atoms is preferable, and an alkyl group having 1-3 carbon atoms is more preferable, with a methyl group being most preferable.

As the acid catalyst, the same catalysts as those listed in the description of Process (1) can be given. The amount of the acid catalyst used is usually 0.0001-2 parts by weight, and preferably 0.001-1 part by weight, for 1 part by weight of the compound of the formula (3).

The compound of the formula (3) can be produced by reacting a compound of the formula (2) with an alcohol of the formula $R^{13}OH$ in the presence of an acid catalyst. The same reaction conditions and the same type of acid catalyst as those mentioned in the description of Process (1) can be used.

(3) Optical Resolution Agent

In the third place, the present invention provides an optical resolution agent comprising at least one 2-oxabicyclo[3.3.0]octane compound of the formula (1).

The optical resolution agent of the present invention preferably comprises at least one 2-oxabicyclo[3.3.0]octane compound of the formula (1), in which the $R^{11}$ is a hydrogen atom, substituted or unsubstituted alkynyl group, substituted or unsubstituted cycloalkyl group, substituted or unsubstituted cycloalkenyl group, substituted or unsubstituted aryl group, substituted or unsubstituted alkoxycarbonyl group, substituted or unsubstituted alkenyloxycarbonyl group, or substituted or unsubstituted aryloxycarbonyl group.

Although the optical resolution agent of the present invention may be a mixture of diastereomers, an optical resolution agent comprising one diastereomer is preferable for simple and efficient optical resolution.

The optical resolution agent of the present invention is useful in the optical resolution of a mixture of optical isomers having an asymmetric carbon atom in the molecule, for example, an alcohol, thiol, carboxylic acid, sulfonic acid, or amine, particularly an optical isomer mixture of alcohol.

It is known that in the compound having a 2-oxabicyclo[3.3.0]octane skeleton of [a five-member ring +a five-member ring], the position 1 substituent and the position 5 substituent are cis-configured (Tetrahedron Lett., 35, 7785 (1994)). Therefore, if $R^1=R^2$, $R^3=R^4$, $R^5=R^6$, $R^7=R^8$, and $R^9=R^{10}$ and $R^{12}$ is an optically active group in the compound of the formula (1), that compound is a mixture of two diastereomers shown in the following formulas (1a) and (1b).

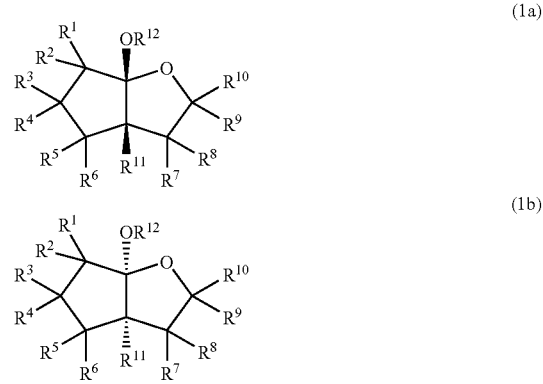

The mixture of the diastereomer of the formula (1a) and the diastereomer of the formula (1b) can be isolated into individual diastereomers by a separation means such as column chromatography, simulated moving bed chromatography, distillation, or crystallization.

(4) Separating Method of Diastereomer Mixture

In the fourth place, the present invention provides a method for separating a diastereomer mixture of 2-oxabicyclo[3.3.0] octane compound (1).

The separating method of the present invention is a method for separating a diastereomer mixture of 2-oxabicyclo [3.3.0] octane compound (1), in which (a) simulated moving bed chromatography or (b) a distilling method is used as a separation means.

(a) Separating Method Using Simulated Moving Bed Chromatography

A simulated moving bed chromatographic separation apparatus is used for the simulated moving bed chromatography. In general, the separating apparatus has a packed bed consisting of several chambers (columns) packed with an adsorbent. The packed bed has a structure to allow a liquid to circulate therein. The packed bed is provided with an eluant feed port, a first component (a strongly adsorbed component) drawing port, a sample feed port, and a second component (a weakly adsorbed component) drawing port in the direction of the liquid flow. The feed ports and drawing ports are caused to intermittently move in the direction of the liquid flow. This operation has the same effect as that achieved by causing the adsorbing layer to move in the direction opposite to the liquid flow. Specifically, this type of apparatus can achieve a high separating performance with the same degree as that obtained by the moving bed chromatography in which separation is effected by causing the adsorbing layer to move. The strongly. adsorbed component refers to a diastereomer that can be adsorbed by the adsorbent more easily than the other diastereomer among at least two diastereomers and the weakly adsorbed component refers to the diastereomer which is adsorbed with a greater difficulty.

Any known adsorbents that can separate the diastereomer mixture into individual streamers can be used as the adsorbent for the simulated moving bed chromatography without any specific limitation. As specific examples of the adsorbent, silica gel, neutral alumina, ion-exchange resin, zeolite, activated carbon, and synthetic adsorbent can be given. The type, average particle diameter, and the filling amount of the adsorbent that can most efficiently separate the diastereomer mixture of the compound of the formula (1) into individual diastereomers can be appropriately selected.

FIG. 1 is a schematic flow chart showing the liquid flow in a simulated moving bed chromatographic separation apparatus used in the present invention. In FIG. 1, 1 indicates an eluant feed port, 2 indicates a first component drawing port, 3 indicates a sample feed port, 4 indicates a second component drawing port, and 5 indicates a circulating liquid. 1a-4a individually indicate the positions of the feed ports and drawing ports 1-4 in an operating period subsequent to a fixed-period operation.

The liquid is circulated in the direction of a column a to a column h using a circulating pump (not shown). The eluant feed port 1, first component drawing port 2, sample feed port 3, and second component drawing port 4 are respectively provided in front of columns a, c, e, and g. In addition, the eluant feed port 1, first component drawing port 2, sample feed port 3, and second component drawing port 4 are respectively provided with a valve (not shown) which can be opened and closed. Opening and closing of the valves can be controlled as the whole separating apparatus. As the valve, an electromagnetic type valve and the like can be given.

After operation for a fixed period of time in this state, the eluant feed port 1, first component drawing port 2, sample feed port 3, and second component drawing port 4 are caused to move along the flow of the circulating liquid 5 to positions in front of the next column, whereby the eluant feed port 1, first component drawing port 2, sample feed port 3, and second component drawing port 4 are respectively shifted to the eluant feed port 1a, first component drawing port 2a, sample feed port 3a, and second component drawing port 4a. The apparatus is operated for a prescribed period of time (an operation switching time). This procedure is repeated.

In order to efficiently separate a diastereomer mixture into individual diastereomers by operating the simulated moving bed chromatographic separation apparatus, the moving speed V1 (V1=length of column/operation switching time) of the eluant feed port 1 and the like should be smaller than the moving speed V2 of the sample in the second component adsorbent, but larger than the moving speed V3 of the sample in the first component adsorbent (V2>V1>V3). Such operating conditions can be established by appropriately selecting the flow rate of liquid in each column, operation switching time, and the type of eluant.

By operating the simulated moving bed chromatographic separation apparatus in this manner, the packed bed can be apparently shifted in the direction reverse to the flowing direction of the circulating liquid 5, whereby it is possible to continuously extract an eluate containing the first component and an eluate containing the second component respectively from the first component drawing port 2 and the second component drawing port 4.

There are no specific limitations to the simulated moving bed chromatographic separation apparatus used in the present invention. The simulated moving bed chromatographic separation apparatuses described in Japanese Patent Applications Laid-open No. 3-168100 and No. 3-134562, for example, can be used.

(b) Separating Method Using Distilling Method

A diastereomer mixture of 2-oxabicyclo[3.3.0]octane compound (1) can also be separated by distillation. Namely, it is possible to selectively collect one of the diastreomers from a solution containing a diastereomer mixture of 2-oxabicyclo[3.3.0]octane compound (1), by condensing the solution under reduced pressure to remove unreacted materials, solvents, and the like optionally, and distilling the resulting residue.

The distillation method is not specifically limited. For example, atmospheric distillation, reduced-pressure distillation, steam distillation, and the like can be used. Of these, reduced-pressure distillation is preferable to increase the separating efficiency while suppressing thermal decomposition of 2-oxabicyclo[3.3.0]octane compound (1) to the minimum. There are no specific limitations to the distillation device. For example, a known distillation device such as a rectification device comprising a rectification column packed with Sulzerpack can be used.

The pressure and temperature of the reduced-pressure distillation are appropriately determined according to the type of the 2-oxabicyclo[3.3.0]octane compound to be separated. The pressure is usually 100-0.001 hPa, preferably 10-0.01 hPa, and more preferably 1-0.05 hPa. The distillation temperature indicated by oil bath temperature is usually 50-250° C., and preferably 70-200° C.

In addition, selectivity of one diastereomer can be increased by increasing the reflux ratio during distillation. The reflux ratio indicates a ratio by weight of the amount of reflux to the amount of distillate (reflux/distillate) and is usually 30/1 or more, preferably 70/1 or more, and more preferably 600/1 or more, and still more preferably 1,200/1 or more.

After selectively collecting only one diastereomer by distillation, the other diastereomers remain in the resulting still residue. The other diastereomers can be purified or isolated by a purification method such as distillation, column chromatography, crystallization, or the like.

Although simulated moving bed chromatography or distillation are preferable methods of separating the diastereomer mixture into individual diastereomers in the present invention, other separating means such as silica gel column chromatography, for example, can be used.

(5) Method of Optically Resolving Alcohol

In the fifth place, the present invention provides a method of optically resolving an optical isomer mixture of alcohol of the formula $R^{14}OH$, wherein $R^{14}$ represents a substituted or unsubstituted hydrocarbon group having an asymmetric carbon atom.

The optical resolution method of the present invention comprises a step of separating a diastereomer mixture of 2-oxabicyclo[3.3.0]octane compound (1) into individual diastereomers (Step A), a step of reacting the separated diastereomers with an alcohol of the formula $R^{13}OH$ in the presence of an acid catalyst to obtain 2-oxabicyclo[3.3.0]octane compound of the above formula (3) (Step B), a step of reacting the 2-oxabicyclo[3.3.0]octane compound of the above formula (3) with an optical isomer mixture of alcohol of the formula $R^{14}OH$ in the presence of an acid catalyst to obtain a diastereomer mixture of 2-oxabicyclo[3.3.0]octane compound of the above formula (4) (Step C), a step of separating the resulting diastereomer mixture into individual diastereomers (Step D), and a step of reacting the separated diastereomers with an alcohol of the formula $R^{15}OH$ in the presence of an acid catalyst to obtain optically active isomers of an alcohol of the formula $R^{14}OH$ (Step E).

This method of optically resolving alcohol will be described in more detail.

(Step A)

First, the diastereomer mixture of 2-oxabicyclo[3.3.0]octane compound (1) is separated into individual diastereomers. Although the above-described methods of using simulated moving bed chromatography, distillation, column chromatography, and the like can be used for the separation in this step, the method of using simulated moving bed chromatography or the distillation method are preferable.

The separated diastereomers of the 2-oxabicyclo[3.3.0]octane compound (1) are compounds shown by the following formulas (1-1) or (1-2). These diastreomers are optically active substances having a steric configuration, in which the position 1 substituent ($R^{11}$) and the position 5 substituent ($OR^{12}$) on the 2-oxabicyclo[3.3.0]octane ring are cis-configured with each other, with either substituent being on the α-plane (or β-plane) with respect to the other.

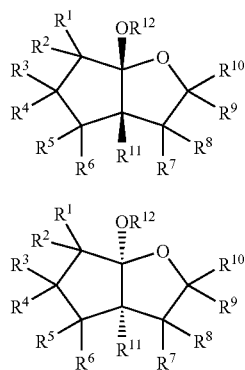

(1-1)

(1-2)

(Step B)

Next, the compound of the formula (1-1) or (1-2) is reacted with an alcohol of the formula $R^{13}OH$ in the presence of an acid catalyst to obtain the compound of the above formula (3). The compound of the above formula (3) is a compound shown by either the following formula (3-1) or (3-2). Since the reaction proceeds while maintaining the steric configuration, the compound of the formula (3-1) is produced from the compound of the formula (1-1) and the compound of the formula (3-2) is produced from the compound of the formula (1-2).

The resulting compounds of the formula (3-1) or (3-2) can be used as an optical resolution agent of alcohol.

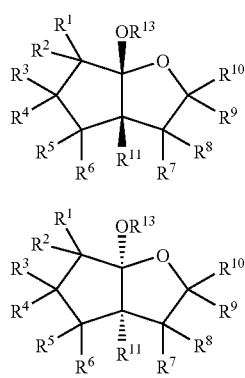

(3-1)

(3-2)

This step may be optionally omitted, in which case the compound of the above formula (1-1) or (1-2) can be used as an optical resolution agent as is.

(Step C)

Next, the compound of the formula (3-1) or (3-2) is reacted with an optical isomer mixture of an alcohol of the formula $R^{14}OH$ in the presence of an acid catalyst to obtain a diastereomer mixture of the compound of the above formula (4). The same reaction conditions and acid catalysts as described in connection with Process 2 for the production of 2-oxabicyclo[3.3.0]octane compound (1) can be used.

The alcohol represented by the formula $R^{14}OH$ is not limited inasmuch as the optical isomer mixture of an alcohol has an asymmetric carbon atom in the molecule. Any alcohol among primary alcohols, secondary alcohols, and tertiary alcohols can be used. As a specific example of the alcohol of the formula $R^{14}OH$, an optical isomer mixture of the same alcohol as the above alcohol (5) can be given.

(Step D)

Next, the resulting diastereomer mixture of the formula (4) is separated into individual diastereomers. The separating method is not specifically limited. Separating methods such as common column chromatography, the above-described simulated moving bed chromatography, the above-described distillation method, and crystallization can be given as examples. Of these, simulated moving bed chromatography and the distillation method are preferable.

(Step E)

Next, the separated diastereomers are reacted with an alcohol of the formula, $R^{15}OH$, wherein $R^{15}$ represents a substituted or unsubstituted hydrocarbon group, in the presence of an acid catalyst to obtain optically active isomers of an alcohol of the formula $R^{14}OH$. The resulting optical active alcohols can be isolated from the reaction solution by a known purification-separation means such as distillation, column chromatography, and the like.

In this instance, if the alcohol of the formula $R^{13}OH$ is used as an alcohol of the formula $R^{15}OH$, the compound of the above formula (3) can be regenerated by isolation and can be reused as an optical resolution agent of alcohol.

EXAMPLES

The present invention will now be described in detail by way of examples, which should not be construed as limiting the present invention. In the examples below "parts" indicates "parts by weight", unless otherwise specified.

Preparation Example 1

Preparation of 2-(2-acetoxyethyl)cyclopentanone 2-(2-Acetoxyethyl)cyclopentanone which is a starting raw material for the preparation of 1-methoxy-2-oxabicyclo [3.3.0]octane was synthesized as described in Tetrahedron Lett., 35, 7785 (1994).

Example 1

Preparation of 1-methoxy-2-oxabicyclo[3.3.0]octane (9)

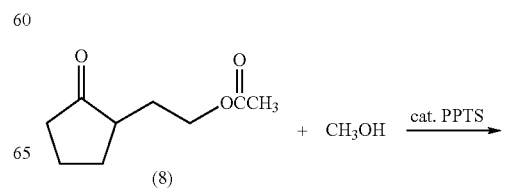

-continued

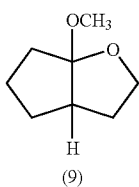

(9)

A reaction vessel was charged with 21 parts of anhydrous toluene, 0.6 parts of methanol, 0.2 part of pyridinium paratoluene sulfonate (PPTS), 2.0 parts of 2-(2-acetoxyethyl)cyclopentanone (8) obtained in Preparation Example 1 at room temperature. The mixture was refluxed for seven hours with stirring. After the reaction, the reaction mixture was filtered and the filtrate was concentrated under reduced pressure. The resulting residue was purified by silica gel column chromatography (n-hexane: ethyl acetate=19:1) to obtain 1.6 parts of 1-methoxy-2-oxabicyclo[3.3.0]octane (9) (yield: 95%).

<Properties of Compound (9)>

EI-MS: m/z 158 (M$^+$)

$^{13}$C-NMR (CDCl$_3$, δ ppm); 24.13, 31.63, 33.79, 34, 86. 47.78, 50.40, 67.86, 120.33

$^1$H-NMR (CDCl$_3$, δ ppm); 1.3-2.5 (m, 9H), 3.20 (s, 3H), 3.72 (dddd,1H), 3.86 (dddd, 1H)

Example 2

Preparation of 5-[((1S)-endo)-(−)-bornyloxy]-2-oxabicyclo[3.3.0]octane (11a, 11b)

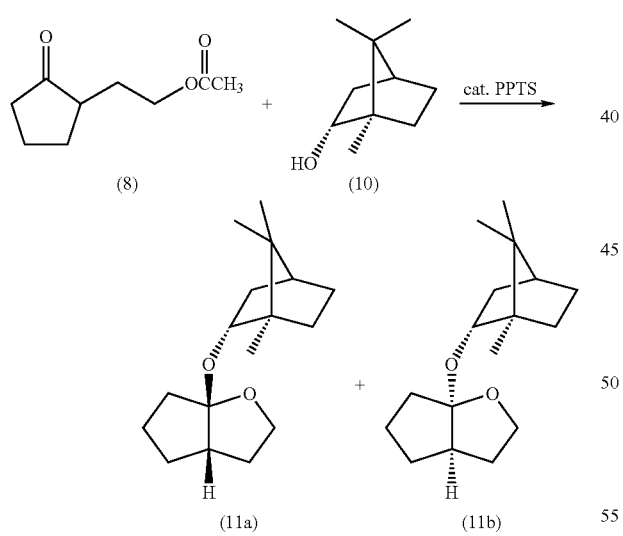

A reaction vessel was charged with 20 parts of 2-(2-acetoxyethyl)cyclopentanone (8) obtained by Preparation Example 1, 2 parts of pyridinium paratoluene sulfonate (PPTS), 18 parts of ((1S)-endo)-(−)-borneol (10), and 200 parts of anhydrous toluene at room temperature. The mixture was refluxed for five hours with stirring. The reaction mixture was filtered and the filtrate was concentrated under reduced pressure. The resulting residue was purified by silica gel column chromatography (n-hexane:diethyl ether=40:1) to obtain 14.7 parts of the target isomer mixture (yield 95%).

The diastereomer mixture obtained was separated into individual diastereomers (11a and 11b) by silica gel column chromatography (n-hexane:diisopropyl ether=1:40).

The properties of the two diastereomers (Isomer 1 and Isomer 2) represented respectively by the formulas (11a) and (11b) are shown below. Among the isomers separated by the silica gel column chromatography, the isomer having a larger Rf value is indicated as Isomer 1 and the isomer having a smaller Rf value is indicated as Isomer 2.

<Properties of Isomer 1>

EI-MS: m/z 264 (M$^+$)

$^{13}$C-NMR (CDCl$_3$, δ ppm); 13.56, 19.00, 19.92, 24.36, 26.72, 28.46, 31.77, 34.19, 36.57, 38.64, 45.46, 47.14, 47.99, 49.09, 67.44, 77.96, 119.96

$^1$H-NMR (CDCl$_3$, δ ppm); 0.70-0.84 (sss, 9H), 0.90-2.48 (m, 16H), 3.68-3.96 (m,3H)

Optical rotation: $[α]_D^{23}$ =−67.38° (c=1.523, CHCl$_3$)

<Properties of Isomer 2>

EI-MS: m/z 264 (M$^+$)

$^{13}$C-NMR (CDCl$_3$, δ ppm); 13.78, 18.92, 19.92, 24.27, 26.69, 28.46, 31.67, 34.36, 36.19, 38.87, 45.24, 47.07, 48.37, 48.84, 67.81, 79.17, 120.82

$^1$H-NMR (CDCl$_3$, δ ppm); 0.70-0.84 (sss, 9H), 0.90-2.48 (m, 16H), 3.68-3.96 (m,3H)

Optical rotation: $[α]_D^{23}$=−1.36° (c=0.525, CHCl$_3$)

Preparation Example 2

Preparation of 2-(2-acetoxyethyl)-2-methoxycarbonylcyclopentanone 2-(2-Acetoxyethyl)-2-methoxycarbonylcyclopentanone (12) was prepared by reacting 2-methoxycarbonylcyclopentanone and 2-iodo ethyl acetate in acetone in the presence of potassium carbonate according to the method described in Tetrahedron Lett., 35, 7785 (1994).

Example 3

Preparation of 1-methoxy-5-methoxycarbonyl-2-oxabicyclo[3.3.0]octane (13)

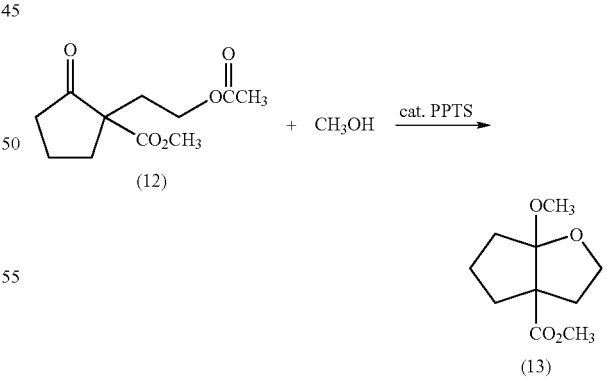

A reaction vessel was charged with 1,580 parts of methanol, 25 parts of PPTS, 228 parts of 2-(2-acetoxyethyl)-2-methoxycarbonylcyclopentanone (12) obtained in Preparation Example 2 at room temperature. The mixture was refluxed for three hours with stirring. After cooling the reaction solution to room temperature, 30 parts of potassium carbonate was added and the mixture was stirred for one hour at room temperature. Insoluble matters were removed by filtration, the filtrate was washed with a brine, and the solvent was evaporated. The residue was distilled under reduced pressure to obtain 167 parts of the target compound (13) (yield: 85%). Boiling point: 68° C./3.5 mmHg <Properties of Compound (13)>

EI-MS: m/z 200(M$^+$)

$^{13}$C-NMR (CDCl$_3$, δ ppm); 22.59, 34.01, 35.71, 37.10, 51.22, 52.04, 62.22, 67.82, 120.33, 174.02

$^1$H-NMR (CDCl$_3$, δ ppm); 1.49-1.89 (m, 5H), 1.96-2.16 (m,1H) m, 2.33-2.48 (m,1H), 2.62-2.78 (m, 1H), 3.2 (s, 3H), 3.64 (s, 3H), 3.82-3.98 (m, 2H)

Preparation Example 3

Preparation of 2-(2-acetoxyethyl)-2-(2-propenyloxy-carbonyl)cyclopentanone

A four-necked flask equipped with a thermometer and a reflux tube was charged with 49.5 parts of 60% sodium hydride, 254 parts of diallyl carbonate, and 711 parts of tetrahydrofuran under a nitrogen stream. The mixture was heated while refluxing. 100 parts of cyclopentanone dissolved in 445 parts of tetrahydrofuran was dropped for one hour, followed by refluxing for three hours. After evaporating the solvent tetrahydrofuran and the produced allyl alcohol from the resulting mixture, 865 parts of toluene and 103 parts of N-methylpyrrolidone were added, and the mixture was heated to 100° C. Then, 264 parts of 2-iodo ethyl acetate was added dropwise for one hour, followed by stirring for one hour at the same temperature. The reaction mixture was cooled and washed with 3% hydrochloric acid aqueous solution and saturated sodium thiosulfate aqueous solution. The solvent was evaporated and the residue was distilled to obtain 258 parts of the target compound (yield: 86%).

Example 4

Preparation of 1-methoxy-5-(2-propenyloxycarbonyl)-2-oxabicyclo[3.3.0]octane (15)

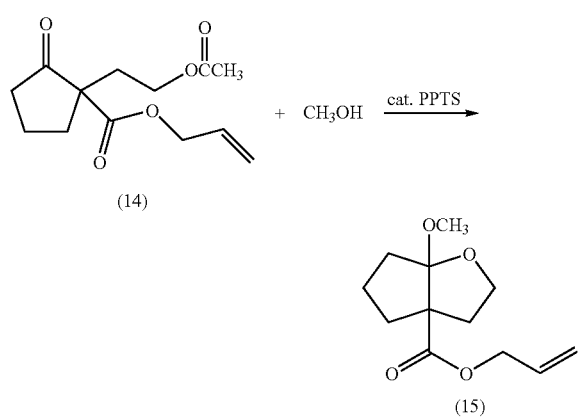

A reaction vessel was charged with 1,580 parts of methanol, 25 parts of PPTS, 254 parts of 2-(2-acetoxyethyl)-2-(2-propenyloxycarbonyl)cyclopentanone (14) obtained in Preparation Example 3 at room temperature. The mixture was refluxed for three hours with stirring. After cooling the reaction solution to room temperature, 30 parts of potassium carbonate was added and the mixture was stirred for one hour at room temperature. Insoluble matters were removed by filtration, the filtrate was washed with saturated brine, and the solvent was evaporated. The residue was distilled under reduced pressure to obtain 146 parts of the target compound (15) (yield: 80%).

Preparation Example 4

Preparation of 1-methoxy-5-(2-propenyl)-2-oxabicyclo[3.3.0]octane 1-methoxy-5-(2-propenyl)-2-oxabicyclo[3.3.0]octane was prepared according to the method described in Tetrahedron Lett., 35, 7785 (1994).

Example 5

Preparation of 1-[((1S)-endo)-(−)-bornyloxy]-5-(2-propenyl)-2-oxabicyclo[3.3.0]octane and separation of diastereomers (18a, 18b)

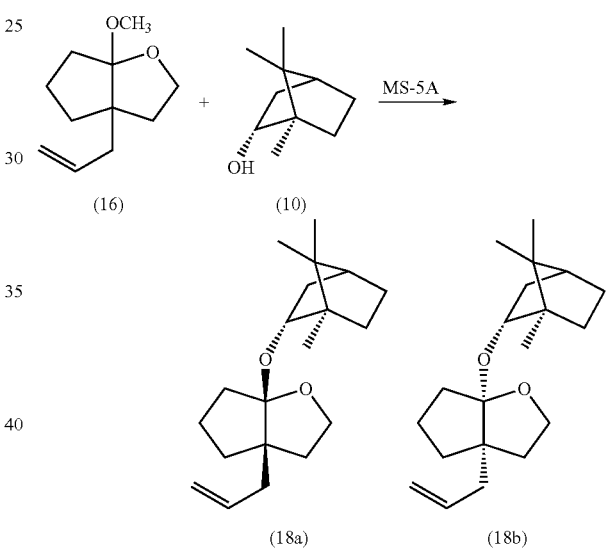

22.8 parts of ((1S)-endo)-(−)-borneol (10) was added to 35 ml of an anhydrous toluene solution containing 30 parts of 1-methoxy-5-(2-propenyl)-2-oxabicyclo[3.3.0]octane (16) and 30 parts of molecular-sieve 5A at room temperature. The mixture was stirred for 10 hours at 110° C. In this instance, 600 parts of molecular-sieve (MS-4A) that can adsorb methanol was filled in the reflux tube to adsorb the methanol generated in the reflux tube. The reaction solution was filtrated. The filtrate was concentrated under reduced pressure to obtain 52 parts of a residue. The resulting residue was purified by silica gel column chromatography (n-hexane:diethyl ether=40:1) to obtain the target isomer mixture. Furthermore, the resulting isomer mixture was separated into individual diastereomers represented by (18a) and (18b) (Isomer 3 and Isomer 4) by silica gel column chromatography (n-hexane: diisopropyl ether=1:40). Isomer 3 (diastereomer having a larger Rf) and Isomer 4 (diastereomer having a smaller Rf) were obtained respectively in an amount of 17.1 parts (yield: 38%) and 18.9 parts (yield: 42%).

The properties of the diastereomers represented by (18a and 18b) are shown as follows.

<Properties of Isomer 3>
Rf (Rf value when developed using n-hexane:toluene=2:1 for a length of 44 mm)
Rf=0.36
EI-MS: m/z 304 (M$^+$)
FT-IR (nujor): 3180, 2960, 2880, 1645, 1480, 1460, 1400, 1375, 1330, 1310, 1240,1195,1125,1060, 1025,960,948, 920cm$^{-1}$
$^1$H-NMR (CDCl$_3$, δ ppm): 0.80 (s, 3H), 0.84 (s, 6H), 0.95-2.22 (m, 16H), 2.27 (m, 1H), 3.98-4.10 (m, 1H), 3.70-3.92 (m, 2H), 5.04-5.09 (m, 2H), 5.88 (ddd, J =7.0, 10.0, 16.5Hz, 1H),
Optical rotation: $[α]_D^{25}=-74.18°$ (c=1.05, CHCl$_3$)

<Properties of Isomer 4>
Rf (Rf value when developed using n-hexane:toluene=2:1 for a length of 44 mm)
Rf=0.28
EI-MS: m/z 304 (M$^+$)
FT-IR (nujor): 3180, 2960, 2880, 1645, 1478, 1460, 1395, 1375, 1325, 1310, 1240, 1195, 1120, 1058, 1025, 960, 948, 920cm$^{-1}$
$^1$H-NMR (CDCl$_3$, δ ppm): 0.80 (s, 3H), 0.84 (s, 6H), 0.95-2.22 (m, 16H), 2.27 (m, 1H), 3.70-3.92 (m, 3H), 5.04-5.09 (m, 2H), 5.88 (ddd, J=7.0, 10.0, 16.5Hz, 1H),
Optical rotation: $[α]_D^{25}=+5.56°$ (c=0.84, CHCl$_3$)

Example 6

Preparation of 1-methoxy-5-(-propenyl)-2-oxabicyclo[3.3.0]octane (16a, 16b)

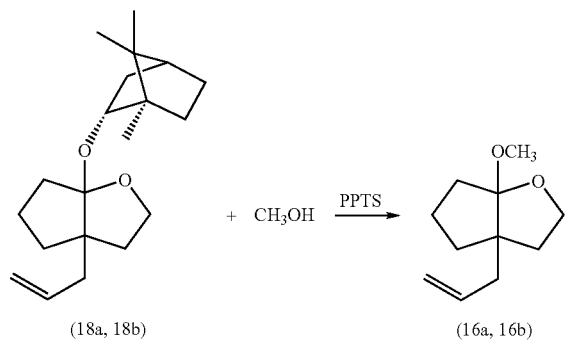

(18a, 18b)    (16a, 16b)

Methanol and PPTS were added to a methylene chloride solution of the diastereomer of 1-[((1S)-endo)-(–)-bornyloxy]-5-(2-propenyl)-2-oxabicyclo[3.3.0]octane (Isomer 3) obtained in Example 5 respectively in an amount of 0.9 mol and 0.1 mol per one mol of the 1-[((1S)-endo)-(–)-bornyloxy]-5-(2-propenyl)-2-oxabicyclo[3.3.0]octane. The mixture was stirred at room temperature for 30 minutes. The reaction solution was washed with saturated brine, dried over anhydrous potassium carbonate, and filtered. The filtrate was concentrated under reduced pressure. The resulting residue was purified by silica gel column chromatography (n-hexane: ethyl acetate=19:1) to obtain the target diastereomer of 1-methoxy-5-(2-propenyl)-2-oxabicyclo[3.3.0]octane (Isomer 5).

The same reaction was carried out using a diastereomer of 1-[((1S)-endo)-(–)-bornyloxy]-5-(2-propenyl)-2-oxabicyclo [3.3.0]octane (Isomer 4) to obtain another diastereomer of 1-methoxy-5-(2-propenyl)-2-oxabicyclo[3.3.0]octane (Isomer 6).

The structures of the diastereomers (Isomer 5 and Isomer 6) of 1-methoxy-5-(2-propenyl)-2-oxabicyclo[3.3.0]octane shown by the formulas (16a) and (16b) were confirmed by measuring FT-IR, $^1$H-NMR, $^{13}$C-NMR, and EI-MS spectrum.

Example 7

Preparation of 1-methoxy-5-n-propyl-2-oxabicyclo[3.3.0]octane (20a, 20b)

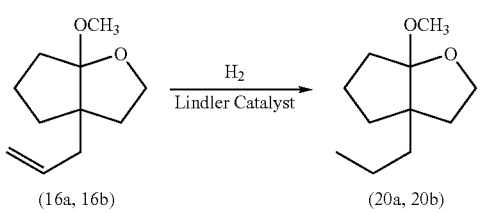

(16a, 16b)    (20a, 20b)

0.01 part of Lindler catalyst (manufactured by Aldrich Co.) was added to a solution of 0.2 part of a diastereomer (Isomer 5) of 1-methoxy-5-(2-propenyl)-2-oxabicyclo[3.3.0]octane obtained in Example 6 in 8 parts of methanol. The hydrogenation reaction was carried out at room temperature in a nitrogen atmosphere under a small hydrogen pressure for two hours. After the reaction, the catalyst was removed by filtration and the filtrate was concentrated under reduced pressure to obtain 0.2 part of one diastreomer (Isomer 7) of the target 1-methoxy-5-n-propyl-2-oxabicyclo[3.3.0]octane as a colorless oil (yield: 96%).

The same reaction was carried out using another diastereomer (Isomer 6) of 1-methoxy-5-(2-propenyl)-2-oxabicyclo [3.3.0]octane obtained in Example 6 to obtain another diastreomer (Isomer 8) of the target 1-methoxy-5-n-propyl-2-oxabicyclo[3.3.0]octane (yield: 95%).

The properties of the two diastereomers (Isomer 7 and Isomer 8) respectively represented by the formulas (20a) and (20b) are as follows.

<Properties of Isomer 7>
EI-MS: m/z 184 (M$^+$)
$^1$H-NMR (CDCl$_3$, δ ppm); 0.90-0.95 (m, 3H), 1.20-1.67 (m, 9H), 1.67-1.75 (m, 1H), 1.84-1.92 (m, 1H), 2.02-2.10 (m, 1H), 3.30 (s, 3H), 3.77-3.84 (m, 2H)
Optical rotaion: $[α]_D^{25}=-47.88°$ (c=0.943, CHCl$_3$)

<Properties of Isomer 8>
EI-MS: m/z 184 (M$^+$)
$^1$H-NMR (CDCl$_3$, δ ppm); 0.88-0.98 (m,3H), 1.20-1.67 (m, 9H), 1.67-1.76 (m, 1H), 1.83-1.92 (m, 1H), 2.02-2.11 (m, 1H), 3.30 (s, 3H), 3.77-3.84 (m, 2H)
Optical rotaion: $[α]_D^{25}=+38.81°$ (c=0.696, CHCl$_3$)

Example 8

Preparation of 1-[((1S)-endo)-(–)-bornyloxy]-5-(2-propenyl)-2-oxabicyclo[3.3.0]octane [(18a), (18b)]

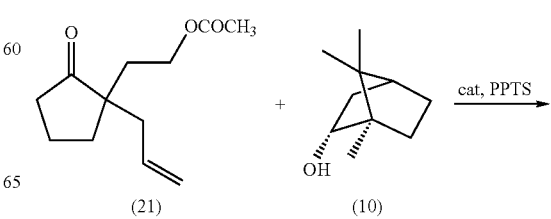

(21)    (10)

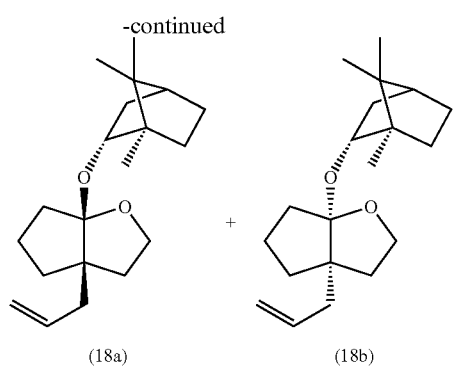

(18a)   (18b)

16.9 parts of ((1S)-endo)-(−)-borneol (10) was added to a solution prepared by adding 21.0 parts of 2-(2-acetoxyethyl)-2-(2-propenyl)cyclopentanone (21) and 2.5 parts of pyridinium paratoluene sulfonate to 173 parts of toluene at room temperature. The mixture was stirred for 10 hours at 110° C. The reaction mixture was filtered and the filtrate was concentrated under reduced pressure. The resulting residue was purified by silica gel column chromatography (n-hexane:diethyl ether=40:1) to obtain 25.9 parts of the target isomer mixture.

The isomer mixture was developed by silica gel thin layer chromatography using a 2:1 mixture of n-hexane and toluene as a developing solution to confirm that the Rf values were 0.28 (Isomer 9) and 0.36 (Isomer 10) when developed for 44 mm.

Example 9

Separation of Diastereomer Mixture Using Simulated Moving Bed Chromatographic Separation Apparatus A part of the isomer mixture obtained in Example 8 was fed to a simulated moving bed chromatographic separation apparatus having eight columns for semi-preparation with an inner diameter of 1 cm and a length of 10 cm packed with silica gel 60N spherical neutral particles (manufactured by Kanto Kagaku) at a flow rate of 0.03 ml/min (concentration: 25 vol %). Operating conditions of the simulated moving bed chromatographic separation apparatus were as follows.

Eluant: 9:1 (by volume) mixture of n-hexane and ethyl acetate
Feed rate of eluant: 2.0 ml/min
Flow rate of strong adsorption component-rich fluid at the drawing port: 1.015 ml/min
Flow rate of weak adsorption component-rich fluid at the drawing port: 1.015 ml/min
Column switching time: 10 min
Temperature: room temperature As a result of separating the above-mentioned isomer mixture after reaching a stationary state under the above conditions, an optically active substance (Isomer 9) with an optical purity of 95% ee was obtained from the drawing port of strong adsorption component-rich fluid. On the other hand, an optically active substance (Isomer 10) with an optical purity of 97% ee was obtained from the drawing port of weak adsorption component-rich fluid. Productivity is shown in Table 1. Productivity is evaluated by the amount of the compound isolated per hour (g/hr).

As a result of measuring EI-MS, FT-IR, $^1$H-NMR, and optical rotation of the resulting Isomers 9 and 10, the Isomer 9 was the same compound as the previously obtained Isomer 4 and the Isomer 10 was the same compound as the previously obtained Isomer 3.

Comparative Example 1

Separation of Diastereomer Mixture Using High Performance Liquid Chromatographic Separation Apparatus A part of the isomer mixture obtained in Example 8 was fed to a high performance liquid chromatographic separation apparatus having eight columns for semi-preparation with an inner diameter of 1 cm and a length of 10 cm packed with silica gel 60N spherical neutral particles (manufactured by Kanto Kagaku). An eluate was collected at the outlet port using a fraction collector. Operating conditions of the high performance liquid chromatographic separation apparatus were as follows.

Eluant: 2:1 (by volume) mixture of n-hexane and toluene
Flow rate: 2.0 ml/min.
Fraction switching time: 5 min An optically active substance with an optical purity of 93% ee was obtained from the drawing port of weak adsorption component-rich fluid of fractions No. 1 to No. 4. An optically active substance with an optical purity of 90% ee was obtained from the drawing port of strong adsorption component-rich fluid of fractions No. 36 to No. 39. Fractions from No. 5 to No. 35 were obtained as mixtures of weak adsorption components and strong adsorption components, which could not be separated. The total period of time required for the processing was 5.2 hours. Productivity is shown in Table 1.

TABLE 1

|  | Example 8 | Comparative Example 1 |
| --- | --- | --- |
| Isomer 9 (g/h) | 0.20 | 0.002 |
| Isomer 10 (g/h) | 0.25 | 0.013 |

The results of Table 1 confirm that the simulated moving bed chromatographic separation apparatus can separate a diastereomer mixture into individual diastereomers continuously and more efficiently as compared with a conventional high performance liquid chromatographic separation apparatus.

Example 10

Preparation of 1-((1S)-ethoxycarbonylethoxy)-5-(2-propenyl)-2-oxabicyclo[3.3.0]octane [(22a), (22b)]

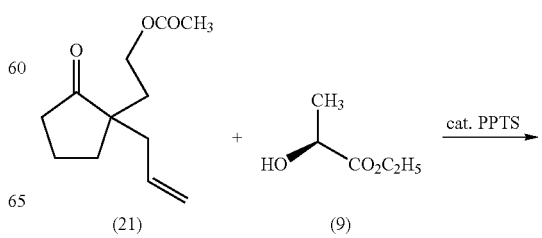

(21)   (9)

-continued (22a)    (22b)

A solution prepared by adding 42.0 parts of 2-(2-acetoxyethyl)-2-(2-propenyl)cyclopentanone (21) to 136 parts of methylene chloride was added dropwise to a solution of 5 parts of PPTS and 26.0 parts of (S)-(−)-ethyl lactate (9) in 200 parts of methylene chloride at 0° C. The mixture was stirred at room temperature for 30 minutes. The reaction solution was washed with saturated brine, dried over anhydrous sodium sulfate, and filtered. The resulting residue obtained by concentrating the filtrate under reduced pressure was purified by silica gel column chromatography using an eluant (n-hexane: diethyl ether=20:1) in an amount of 50 times by weight of the residue to obtain 46.6 parts of a mixture of isomers of the formulas (22a) and (22b).

The isomer mixture was developed by silica gel thin layer chromatography using a 4:1 mixture of n-hexane and diisopropyl ether as a developing solution to confirm that the Rf values were 0.32 (Isomer 11) and 0.41 (Isomer 12) when developed for 69 mm.

As a result of separating the above-mentioned isomer mixture using the same simulated moving bed chromatographic separation apparatus as that used in Example 9 after reaching a stationary state under the same conditions as in Example 9, an optically active substance (Isomer 11) with an optical purity of 96% ee was obtained from the drawing port of strong adsorption component-rich fluid. On the other hand, an optically active substance (Isomer 12) with an optical purity of 98% ee was obtained from the drawing port of weak adsorption component-rich fluid.

The properties of the resulting isomers are as follows.

<Properties of Isomer 11>

EI-MS: m/z 268 ($M^+$)

FT-IR (Nujor); 3060, 2980, 2950, 2930, 2870, 1755, 1738, 1640, 1450, .1375, 1300, 1270, 1185, 1140, 1130, 1120, 950, 915 $cm^{-1}$ $^1$H-NMR (CDCl$_3$, δ ppm); 1.27-1.71 (m, 12H), 2.00 (m, 1H), 2.01-2.16 (m, 2H), 2.17-2.39 (m, 1H), 3.75-3.79 (m, 2H), 4.14-4.20 (m, 3H), 5.03-5.10 (m, 2H), 5.90 (ddd, 1H), Optical rotation: $[\alpha]_D^{25}$=−0.10° (c=5.50, CHCl$_3$)

<Properties of Isomer 12>

EI-MS: m/z 268 ($M^+$)

FT-IR (Nujor); 3065, 2970, 2960, 2880, 1755, 1740, 1645, 1455, 1365, 1310, 1275, 1190, 1125, 1045, 915 $cm^{-1}$ $^1$H-NMR (CDCl$_3$, δ ppm); 1.26-1.75 (m, 12H), 1.93-1.96 (m, 2H), 2.21-2.28 (m, 2H), 3.78-3.86 (m, 2H), 4.15-4.20 (m, 2H), 4.37-4.38 (m, 1H), 5.02-5.09 (m, 2H), 5.91 (ddd, 1H)

Optical rotation: $[\alpha]_D^{25}$=−74.75° (c=8.85, CHCl$_3$)

Example 11

Preparation of 5-(2-propenyl)-1-((1S)-ethoxycarbonylethoxy)-2-oxabicyclo[3.3.0]octane [(22a), (22b)]

(16)    (9)

(22a)    (22b)

10.6 parts (S)-(−)-ethyl lactate (9) and 18.2 parts of molecular sieve (MS-5A) were added to 184 parts of anhydrous toluene. After the addition of 18.2 parts of 1-methoxy-5-(2-propenyl)-2-oxabicyclo[3.3.0]octane at room temperature, the resulting mixture was refluxed for seven hours. In this instance, 364 parts of molecular sieve (MS-4A) that can adsorb methanol was filled in the reflux tube to adsorb the methanol in the reflux tube. After the reaction, the reaction solution was filtered. The filtrate was concentrated under reduced pressure and the resulting residue was distilled under reduced pressure using a 9-plate mini-throughther (manufactured by Tokaseiki Co., Ltd.). The unreacted compound (9) was first collected, then the unreacted compound (16) was collected. Then, the diastereomer mixture was separated by distillation. The distillation conditions were as follows.

<Conditions for Collecting Unreacted Compound (16)>

Oil bath temperature: 140° C.

Still temperature: 110° C.

Column top temperature: 50.4° C./1.0 mmHg

Reflux ratio: (Reflux amount)/(Distillate amount)=10/1 (by weight)

<Isomer Mixture Separating Conditions>

Oil bath temperature: 164° C.

Still temperature: 132° C.

Column top temperature: 104.6° C./1.0 mmHg

Reflux ratio: (reflux amount)/(distillate amount) was changed in the order of 30/1→70/1→600/1→1200/1

The distilled product was a mixture of the Isomer 13 and Isomer 14.

The results of analysis by gas chromatography of distillate components when the ratio (reflux amount: distillate amount) was 1:30, 1:70, 1:600, or 1:1200 is shown in Table 2.

TABLE 2

|  | Reflux ratio 1:30 | Reflux ratio 1:70 | Reflux ratio 1:600 | Reflux ratio 1:1200 |
|---|---|---|---|---|
| Isomer 13 | 40 | 35 | 25 | 5 |
| Isomer 14 | 60 | 65 | 75 | 95 |

The results of Table 2 confirmed that if a diastereomer mixture (a mixture of Isomer 13 and Isomer 14) respectively represented by the formulas (22a) and (22b) is distilled under reduced pressure, one of the diastereomers (Isomer 14 in this Example) can be selectively isolated. It was further confirmed that the higher the reflux ratio, the higher the selectivity of isolation of Isomer 14 by distillation.

As a result of measuring EI-MS, FT-IR, $^1$H-NMR, and optical rotation of the resulting Isomers 13 and 14, the Isomer 13 was the same compound as the previously obtained Isomer 11 and the Isomer 14 was the same compound as the previously obtained Isomer 12.

Example 12

Optical Resolution of 2-octanol (Optical Isomer Mixture)

(1) Preparation of Optically Active 1-methoxy-5-(2-propenyl)-2-oxabicyclo[3.3.0]octane 300 parts of one of the diastereomers of 1-[((1S)-endo)-(−)-bornyloxy]-5-(2-propenyl)-2-oxabicyclo[3.3.0]octane (isomer having a larger RF) obtained in Example 9 was dissolved in 3,000 parts of anhydrous methanol, and 30 parts of PPTS was added. The mixture was refluxed for 12 hours. After cooling to room temperature, 60 parts of potassium carbonate was added to the reaction solution and the mixture was stirred for 15 minutes. The reaction solution was poured into water. The mixture was extracted with diethyl ether three times. The organic layer was combined, dried over anhydrous magnesium sulfate, and filtered. The filtrate was concentrated under-reduced pressure and the resulting residue was purified by silica gel column chromatography (n-hexane:ethyl acetate=10:1) to obtain 166 parts of a target product. The yield was 92%.

(2) Preparation of Diastereomer Mixture of 1-(2-octyloxy)-5-(2-propenyl)-2-oxabicyclo[3.3.0]octane A reaction vessel was charged with 870 parts of anhydrous toluene, 54 parts of an optical isomer mixture of 2-octanol, 80 parts of molecular sieve (MS-5A), and 80 parts of 1-methoxy-5-(2-propenyl)-2-oxabicyclo[3.3.0]octane obtained in (1) above at room temperature. The mixture was refluxed for five hours with stirring. In this instance, the reaction vessel was equipped with a reflux tube packed with 160 parts of molecular-sieve (MS-4A) that can adsorb methanol to adsorb the methanol generated in the reaction system. After the reaction, the reaction solution was filtered and the filtrate was concentrated under reduced pressure to obtain 117 parts of the target diastereomer mixture of 1-(2-octyloxy)-5-(2-propenyl)-2-oxabicyclo[3.3.0]octane. The yield was 95%.

The diastereomer mixture was identified by measurement of the FT-IR, $^1$H-NMR spectrum, and $^{13}$C-NMR spectrum.

(3) Separation of Diastereomer Mixture of 1-(2-octyloxy)-5-(2-propenyl)-2-oxabicyclo[3.3.0]octane 110 parts of the diastereomer mixture of 1-(2-octyloxy)-5-(2-propenyl)-2-oxabicyclo[3.3.0]octane prepared in (2) above was separated into individual diastereomers using the same technique of simulated moving bed chromatography as that used in Example 9.

As a result of separating the isomer mixture after reaching a stationary state, an optically active substance (Isomer 15) with an optical purity of 96% ee was obtained from the drawing port of strong adsorption component-rich fluid. On the other hand, an optically active substance (Isomer 16) with an optical purity of 98% ee was obtained from the drawing port of weak adsorption component-rich fluid. The productivity was 0.5 g/h in the case of Isomer 15 and 0.45 g/h in the case of Isomer 16.

(4) Isolation of Optically Active 2-octanol 175 parts of one diastereomer (Isomer 15) was dissolved in 4,000 parts of anhydrous methanol and 16 parts of pyridinium p-toluenesulfonate (PPTS) was added. Then, the mixture was refluxed for 12 hours. After cooling to room temperature, 20 parts of potassium carbonate was added to the reaction solution and the mixture was stirred for 15 minutes. The reaction solution was poured into water. The mixture was extracted with diethyl ether three times. The organic layer was combined, dried over anhydrous sodium sulfate, and filtered. The filtrate was concentrated under reduced pressure. The resulting residue was purified by silica gel column chromatography (n-hexane:ethyl acetate=10:1) to obtain 95 parts (yield 94%) of the target optically active 2-octanol and 108 parts (yield 96%) of 1-methoxy-5-(2-propenyl)-2-oxabicyclo[3.3.0]octane.

The same procedure as above was carried out for another diastereomer (Isomer 16) with to obtain the other optically active 2-octanol (yield 94%). At the same time, 1-methoxy-5-(2-propenyl)-2-oxabicyclo[3.3.0]octane was collected (yield 95%).

The optical rotation of the resulting optically active 2-octanols were as follows.

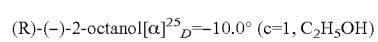

The optical rotation of the resulting optically active 2-octanols showed good agreement with the known data, indicating that optical resolution was successful.

INDUSTRIAL APPLICABILITY

According to the present invention, an optical isomer mixture of a compound such as alcohol can be optically resolved using a simple method and a novel 2-oxabicyclo[3.3.0]octane compound which can be used as an optical resolution agent with high versatility can be provided.

According to the present invention, an optical resolution agent (a 2-oxabicyclo[3.3.0]octane compound) which can optically resolve an alcohol having an asymmetric carbon atom in the molecule in a simple manner can be provided.

According to the present invention, the 2-oxabicyclo[3.3.0]octane compound of the present invention can be produced in a high yield using a simple process of reacting an easily available cyclopentanone compound with an alcoholic compound.

According to the present invention, the compound of the present invention can be produced in a high yield by a short path.

According to the method for separating a diastereomer mixture using the simulated moving bed chromatography of the present invention, an optically active substance (diastereomer) with a high optical purity can be obtained efficiently and continuously. Since a wide variety of solvents can be used as an eluant, the method has excellent generality and versatility. According to the method for separating a diastereomer mixture by distillation of the present invention, an optically active substance (diastereomer) with a high optical purity can be obtained efficiently and continuously.

According to the optical resolution method of the present invention, an optical isomer mixture of alcohol can be certainly separated in a simple manner.

The invention claimed is:

1. A 2-oxabicyclo[3.3.0]octane compound of the following formula (1),

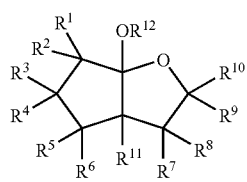

wherein $R^1$-$R^{10}$ individually represent a hydrogen atom or a substituted or unsubstituted alkyl group having 1-20 carbon atoms, $R^{11}$ represents a hydrogen atom, a substituted or unsubstituted alkyl group, a substituted or unsubstituted alkynyl group, a substituted or unsubstituted cycloalkyl group, a substituted or unsubstituted cycloalkenyl group, a substituted or unsubstituted aryl group, formyl group, a substituted or unsubstituted acyl group, a substituted or unsubstituted alkoxycarbonyl group, a substituted or unsubstituted alkenyloxycarbonyl group, a substituted or unsubstituted aryloxycarbonyl group, or a substituted or unsubstituted alkenyl group, and $R^{12}$ represents a substituted or unsubstituted chiralic secondary hydrocarbon group.

2. A 2-oxabicyclo[3.3.0]octane compound of the following formula (1),

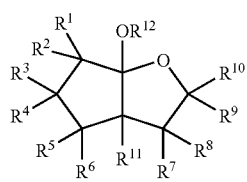

wherein $R^1$-$R^{10}$ individually represent a hydrogen atom or a substituted or unsubstituted alkyl group having 1-20 carbon atoms, $R^{11}$ represents a hydrogen atom, a substituted or unsubstituted alkyl group, a substituted or unsubstituted alkynyl group, a substituted or unsubstituted cycloalkyl group, a substituted or unsubstituted cycloalkenyl group, a substituted or unsubstituted aryl group, formyl group, a substituted or unsubstituted acyl group, a substituted or unsubstituted alkoxycarbonyl group, a substituted or unsubstituted alkenyloxycarbonyl group, a substituted or unsubstituted aryloxycarbonyl group, or a substituted or unsubstituted alkenyl group, and $R^{12}$ represents a chiralic secondary hydrocarbon group having a crosslinked structure or a chiralic secondary alkyl group substituted with an alkoxycarbonyl group.

3. A process for producing a 2-oxabicyclo[3.3.0]octane compound comprising reacting a cyclopentanone compound of the formula (2),

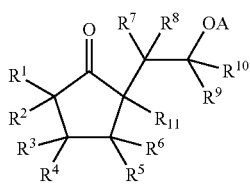

wherein $R^1$-$R^{10}$ individually represent a hydrogen atom or a substituted or unsubstituted alkyl group having 1-20 carbon atoms, $R^{11}$ represents a hydrogen atom, a substituted or unsubstituted alkyl group, a substituted or unsubstituted alkynyl group, a substituted or unsubstituted cycloalkyl group, a substituted or unsubstituted cycloalkenyl group, a substituted or unsubstituted aryl group, formyl group, a substituted or unsubstituted acyl group, a substituted or unsubstituted alkoxycarbonyl group, a substituted or unsubstituted alkenyloxycarbonyl group, a substituted or unsubstituted aryloxycarbonyl group, or a substituted or unsubstituted alkenyl group, and A is a hydrogen atom or a protective group for a hydroxyl group, with an optically active alcohol of the formula $R^{12}OH$, wherein $R^{12}$ represents a substituted or unsubstituted hydrocarbon group, provided that when $R^{11}$ is a substituted or unsubstituted alkenyl group, $R^{12}$ is a chiral group, in the presence of an acid catalyst.

4. A process for producing a 2-oxabicyclo[3.3.0]octane compound comprising reacting a 2-oxabicyclo[3.3.0]octane compound of the formula (3),

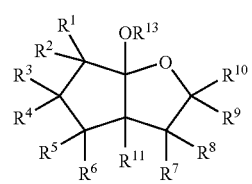

wherein $R^1$-$R^{10}$ individually represent a hydrogen atom or a substituted or unsubstituted alkyl group having 1-20 carbon atoms, $R^{11}$ represents a hydrogen atom, a substituted or unsubstituted alkyl group, a substituted or unsubstituted alkynyl group, a substituted or unsubstituted cycloalkyl group, a substituted or unsubstituted cycloalkenyl group, a substituted or unsubstituted aryl group, formyl group, a substituted or unsubstituted acyl group, a substituted or unsubstituted alkoxycarbonyl group, a substituted or unsubstituted alkenyloxycarbonyl group, a substituted or unsubstituted aryloxycarbonyl group, or a substituted or unsubstituted alkenyl group and $R^{13}$ is a substituted or unsubstituted hydrocarbon group, with an alcohol of the formula $R^{12}OH$, wherein $R^{12}$ represents a substituted or unsubstituted hydrocarbon group, provided that when $R^{11}$ is a substituted or unsubstituted alkenyl group, $R^{12}$ is a chiral group, in the presence of an acid catalyst.

5. A method for separating a diastereomer mixture of 2-oxabicyclo [3.3.0]octane compounds of the following formula (1),

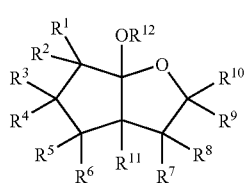

wherein $R^1$-$R^{10}$ individually represent a hydrogen atom or a substituted or unsubstituted alkyl group having 1-20 carbon atoms, $R^{11}$ represents a hydrogen atom, a substituted or unsubstituted alkyl group, a substituted or unsubstituted alkynyl group, a substituted or unsubstituted cycloalkyl group, a substituted or unsubstituted cycloalkenyl group, a substituted or unsubstituted aryl group, formyl group, a substituted or unsubstituted acyl group, a substituted or unsubstituted alkoxycarbonyl group, a substituted or unsubstituted alkenyloxycarbonyl group, a substituted or unsubstituted aryloxycarbonyl group, or a substituted or unsubstituted alkenyl group, and $R^{12}$ represents a substituted or unsubstituted chiralic secondary hydrocarbon group, comprising processing the diastereomer mixture of 2-oxabicyclo [3.3.0]octane compounds of the formula (1) using a simulated moving bed chromatography to separate into individual diastereomers.

6. A method for separating a diastereomer mixture of 2-oxabicyclo [3.3.0]octane compounds of the following formula (1),

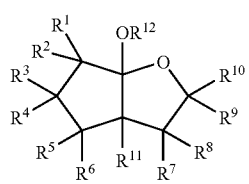

(1)

wherein $R^1$-$R^{10}$ individually represent a hydrogen atom or a substituted or unsubstituted alkyl group having 1-20 carbon atoms, $R^{11}$ represents a hydrogen atom, a substituted or unsubstituted alkyl group, a substituted or unsubstituted alkynyl group, a substituted or unsubstituted cycloalkyl group, a substituted or unsubstituted cycloalkenyl group, a substituted or unsubstituted aryl group, formyl group, a substituted or unsubstituted acyl group, a substituted or unsubstituted alkoxycarbonyl group, a substituted or unsubstituted alkenyloxycarbonyl group, a substituted or unsubstituted aryloxycarbonyl group, or a substituted or unsubstituted alkenyl group, and $R^{12}$ represents a substituted or unsubstituted chiralic secondary hydrocarbon group, comprising distilling the diastereomer mixture of 2-oxabicyclo [3.3.0]octane compounds of formula (1) to separate into individual diastereomers.

7. A method for optically resolving alcohol of the formula $R^{14}OH$, wherein $R^{14}$ represents a substituted or unsubstituted hydrocarbon group having an asymmetric carbon atom, comprising, a step of separating a diastereomer mixture of 2-oxabicyclo [3.3.0]octane compounds of the following formula (1),

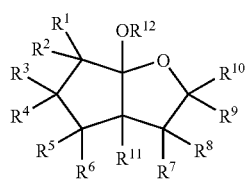

(1)

wherein $R^1$-$R^{10}$ individually represent a hydrogen atom or a substituted or unsubstituted alkyl group having 1-20 carbon atoms, $R^{11}$ represents a hydrogen atom, a substituted or unsubstituted alkyl group, a substituted or unsubstituted alkynyl group, a substituted or unsubstituted cycloalkyl group, a substituted or unsubstituted cycloalkenyl group, a substituted or unsubstituted aryl group, formyl group, a substituted or unsubstituted acyl group, a substituted or unsubstituted alkoxycarbonyl group, a substituted or unsubstituted alkenyloxycarbonyl group, a substituted or unsubstituted aryloxycarbonyl group, or a substituted or unsubstituted alkenyl group, and $R^{12}$ represents a substituted or unsubstituted chiralic secondary hydrocarbon group, a step of reacting one of the separated diastereomers with an alcohol of the formula $R^{13}OH$, wherein $R^{13}$ is a substituted or unsubstituted hydrocarbon group, in the presence of an acid catalyst to obtain a 2-oxabicyclo[3.3.0] octane compound of the formula (3),

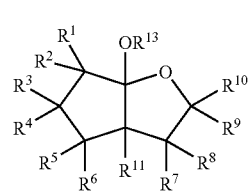

(3)

wherein $R^1$-$R^{11}$ are the same as in the formula (1) and $R^{13}$ is as defined above, a step of reacting the compound of the formula (3) with an optical isomer mixture of alcohol of the formula $R^{14}OH$, wherein $R^{14}$ is as defined above, in the presence of an acid catalyst to obtain a diastereomer mixture of the formula (4),

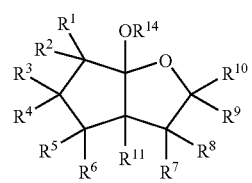

(4)

wherein $R^1R^{11}$ and $R^{14}$ are the same as defined above, a step of separating the resulting diastereomer mixture into individual diastereomers, and a step of reacting one of the separated diastereomers with an alcohol of the formula $R^{15}OH$, wherein $R^{15}$ represents a substituted or unsubstituted hydrocarbon group, in the presence of an acid catalyst to obtain an optically active alcohol of the formula $R^{14}OH$, wherein $R^{14}$ is as defined above.

8. The method according to claim 7, wherein the step of separating the diastereomer mixture of the compound of the above formula (4) into individual diastereomers comprises processing the diastereomer mixture using simulated moving bed chromatography to separate into individual diastereomers.

9. The method according to claim 7, wherein the step of separating the diastereomer mixture of the compound of the above formula (4) into individual diastereomers comprises distilling the diastereomer mixture to separate into individual diastereomers.

10. The method according to claim 9, wherein the optical active alcohol of the formula $R^{14}OH$, wherein $R^{14}$ is as defined above, and the compound of the above formula (3) are isolated by reacting the separated diastereomer of the compound of the formula (4) with an alcohol of the formula $R^{13}OH$, wherein $R^{13}$ is as defined above, in the presence of an acid catalyst, and the isolated compound of the formula (3) is reused as an optical resolution agent of alcohol.

11. The method according to claim 7 wherein the optical active alcohol of the formula $R^{14}OH$, wherein $R^{14}$ is as defined above, and the compound of the above formula (3) are isolated by reacting the separated diastereomer of the compound of the formula (4) with an alcohol of the formula $R^{13}OH$, wherein $R^{13}$ is as defined above, in the presence of an acid catalyst, and the isolated compound of the formula (3) is reused as an optical resolution agent of alcohol.

12. The method according to claim 10, wherein the optical active alcohol of the formula $R^{14}OH$, wherein $R^{14}$ is as defined above, and the compound of the above formula (3) are isolated by reacting the separated diastereomer of the compound of the formula (4) with an alcohol of the formula $R^{13}OH$, wherein $R^{13}$ is as defined above, in the presence of an acid catalyst, and the isolated compound of the formula (3) is reused as an optical resolution agent of alcohol.

* * * * *